United States Patent
Arbeit et al.

(10) Patent No.: US 11,219,621 B2
(45) Date of Patent: *Jan. 11, 2022

(54) METHODS FOR TREATING IMMUNODEFICIENCY DISEASE

(71) Applicant: X4 Pharmaceuticals, Inc., Boston, MA (US)

(72) Inventors: Robert D. Arbeit, West Newton, MA (US); Paula Marie Ragan, Belmont, MA (US)

(73) Assignee: X4 Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/804,863

(22) Filed: Feb. 28, 2020

(65) Prior Publication Data

US 2020/0268739 A1 Aug. 27, 2020

Related U.S. Application Data

(63) Continuation of application No. 16/065,470, filed as application No. PCT/US2016/068394 on Dec. 22, 2016, now Pat. No. 10,610,527.

(Continued)

(51) Int. Cl.
*A61K 31/4709* (2006.01)
*A61K 9/48* (2006.01)
(Continued)

(52) U.S. Cl.
CPC ........ *A61K 31/4709* (2013.01); *A61K 9/0053* (2013.01); *A61K 9/485* (2013.01);
(Continued)

(58) Field of Classification Search
CPC .. A61K 31/4709; A61K 9/0053; A61K 9/485; A61K 9/4858; A61K 9/4866;
(Continued)

(56) References Cited

U.S. PATENT DOCUMENTS 4,933,447 A 6/1990 Konno et al.
5,021,409 A 6/1991 Murrer et al.
(Continued)

FOREIGN PATENT DOCUMENTS

EP 0434385 6/1991
WO WO-1997009976 3/1997
(Continued)

OTHER PUBLICATIONS

"Common Terminology Criteria for Adverse Events (CTCAE), Version 4.0," U.S. Department of Health and Human Services, National Institutes of Health, National Cancer Institute, NIH Publication No. 09-5410, May 28, 2009, revised Jun. 2010 (196 pages).

(Continued)

*Primary Examiner* — Savitha M Rao
(74) *Attorney, Agent, or Firm* — Andrea L. C. Reid; Dechert LLP

(57) ABSTRACT

The present invention relates to methods of treating patients with WHIM syndrome or related disorders, such as myelokathexis, in which X4P-001 is administered in order to reduce the activity of CXCR4. The methods demonstrate surprising effectiveness, with comparatively little toxicity.

19 Claims, 9 Drawing Sheets

Related U.S. Application Data

(60) Provisional application No. 62/428,964, filed on Dec. 1, 2016, provisional application No. 62/271,087, filed on Dec. 22, 2015.

(51) Int. Cl.

| | |
|---|---|
| *C07D 235/14* | (2006.01) |
| *A61K 9/00* | (2006.01) |
| *C07D 401/04* | (2006.01) |
| *C07D 401/12* | (2006.01) |
| *A61P 37/04* | (2006.01) |
| *A61P 17/12* | (2006.01) |
| *A61K 31/395* | (2006.01) |

(52) U.S. Cl.
CPC .......... *A61K 9/4858* (2013.01); *A61K 9/4866* (2013.01); *A61K 31/395* (2013.01); *A61P 17/12* (2018.01); *A61P 37/04* (2018.01); *C07D 235/14* (2013.01); *C07D 401/04* (2013.01); *C07D 401/12* (2013.01)

(58) Field of Classification Search
CPC ........ A61P 17/12; A61P 37/04; C07D 235/14; C07D 401/04; C07D 401/12
See application file for complete search history.

(56) References Cited

U.S. PATENT DOCUMENTS

| | | | |
|---|---|---|---|
| 5,235,056 A | 8/1993 | Cunkle et al. | |
| 5,563,151 A | 10/1996 | Bowles et al. | |
| 5,582,823 A | 12/1996 | Souza et al. | |
| 5,583,131 A | 12/1996 | Bridger et al. | |
| 5,698,546 A | 12/1997 | Bridger et al. | |
| 5,817,807 A | 10/1998 | Bridger et al. | |
| 5,932,749 A | 8/1999 | Li et al. | |
| 6,001,826 A | 12/1999 | Murrer et al. | |
| 6,245,799 B1 | 6/2001 | Asseslin et al. | |
| 6,268,354 B1 | 7/2001 | Nishimura et al. | |
| 6,365,583 B1 | 4/2002 | MacFarland et al. | |
| 6,506,770 B1 | 1/2003 | Bridger et al. | |
| 6,552,065 B2 | 4/2003 | Remiszewski et al. | |
| 6,635,278 B1 | 10/2003 | Dahl et al. | |
| 6,683,192 B2 | 1/2004 | Baxter et al. | |
| 6,734,191 B2 | 5/2004 | Bridger et al. | |
| 6,734,194 B2 | 5/2004 | End et al. | |
| 6,794,379 B2 | 9/2004 | Medina et al. | |
| 6,825,351 B2 | 11/2004 | McEachern et al. | |
| 6,835,731 B2 | 12/2004 | Bridger et al. | |
| 6,864,265 B2 | 3/2005 | Bridger et al. | |
| 6,878,714 B2 | 4/2005 | Askew et al. | |
| 6,987,102 B2 | 1/2006 | Bridger et al. | |
| 7,053,215 B2 | 5/2006 | Medina et al. | |
| 7,091,217 B2 | 8/2006 | Bridger et al. | |
| 7,135,570 B2 | 11/2006 | McEachern et al. | |
| 7,169,750 B2 | 1/2007 | Bridger et al. | |
| 7,291,631 B2 | 11/2007 | Bridger et al. | |
| 7,332,605 B2 | 2/2008 | Crawford et al. | |
| 7,354,932 B2 | 4/2008 | Bridger et al. | |
| 7,354,934 B2 | 4/2008 | Bridger et al. | |
| 7,452,994 B2 | 11/2008 | McEachern et al. | |
| 7,491,544 B2 | 2/2009 | Canary et al. | |
| 7,501,518 B2 | 3/2009 | Chen et al. | |
| 7,550,484 B2 | 6/2009 | Bridger et al. | |
| 7,592,351 B2 | 9/2009 | Sundermann et al. | |
| 7,723,525 B2 | 5/2010 | Crawford et al. | |
| 7,863,293 B2 | 1/2011 | Bridger et al. | |
| 7,897,590 B2 | 3/2011 | Bridger et al. | |
| 7,935,692 B2 | 5/2011 | Bridger et al. | |
| 8,168,783 B2 | 5/2012 | Kokubo et al. | |
| 8,178,123 B2 | 5/2012 | Pauletti et al. | |
| 8,778,967 B2 | 7/2014 | Bridger et al. | |
| 8,889,159 B2 | 11/2014 | Cleary et al. | |
| 8,906,682 B2 | 12/2014 | June et al. | |
| 9,119,790 B2 | 9/2015 | Crowley et al. | |
| 9,155,723 B2 | 10/2015 | Jain et al. | |
| 9,267,934 B2 | 2/2016 | Singh et al. | |
| 9,314,468 B2 | 4/2016 | Clark et al. | |
| 10,548,889 B1 | 2/2020 | Brands | |
| 10,610,527 B2 | 4/2020 | Arbeit et al. | |
| 2003/0220341 A1 | 11/2003 | Bridger et al. | |
| 2003/0232808 A1 | 12/2003 | Kobayashi et al. | |
| 2005/0154201 A1 | 7/2005 | Chen et al. | |
| 2005/0227958 A1 | 10/2005 | Wang et al. | |
| 2007/0123538 A1 | 5/2007 | Dunkle et al. | |
| 2007/0167459 A1 | 7/2007 | Habashita et al. | |
| 2007/0232615 A1 | 10/2007 | Gudmundsson et al. | |
| 2008/0045537 A1 | 2/2008 | Gudmundsson et al. | |
| 2008/0058353 A1 | 3/2008 | Banks | |
| 2008/0096861 A1 | 4/2008 | Gudmundsson et al. | |
| 2008/0167341 A1 | 7/2008 | Bridger et al. | |
| 2008/0171740 A1 | 7/2008 | Gudmundsson et al. | |
| 2009/0203533 A1 | 8/2009 | Munnes et al. | |
| 2009/0247570 A1 | 10/2009 | Mayer | |
| 2009/0325877 A1 | 12/2009 | Grunt et al. | |
| 2010/0002272 A1 | 1/2010 | Sato et al. | |
| 2010/0022724 A1 | 1/2010 | Jacobsen et al. | |
| 2010/0143301 A1 | 6/2010 | Desai et al. | |
| 2011/0206607 A1 | 8/2011 | Olsson et al. | |
| 2011/0293521 A1 | 12/2011 | Hyde et al. | |
| 2012/0041028 A1 | 2/2012 | Cooper et al. | |
| 2012/0141471 A1 | 6/2012 | Salvino et al. | |
| 2013/0216531 A1 | 8/2013 | Jain et al. | |
| 2014/0275260 A1 | 9/2014 | Kawale, Sr. et al. | |
| 2015/0004239 A1 | 1/2015 | Cullen et al. | |
| 2015/0030561 A1 | 1/2015 | Dale et al. | |
| 2015/0216843 A1 | 8/2015 | Fearon et al. | |
| 2015/0246019 A1 | 9/2015 | Bridger et al. | |
| 2015/0301058 A1 | 10/2015 | Schettini et al. | |
| 2015/0352208 A1 | 12/2015 | Fearon et al. | |
| 2016/0089385 A1 | 3/2016 | Sherman et al. | |
| 2017/0090658 A1 | 3/2017 | Park et al. | |
| 2017/0166591 A1 | 6/2017 | Ojima et al. | |
| 2017/0234879 A1 | 8/2017 | Klinguer-Hamour et al. | |
| 2018/0228894 A1 | 8/2018 | Fearon | |
| 2018/0369167 A1 | 12/2018 | Arbeit et al. | |
| 2018/0369229 A1 | 12/2018 | Ragan et al. | |
| 2019/0030023 A1 | 1/2019 | Arbeit et al. | |
| 2019/0083485 A1 | 3/2019 | Arbeit et al. | |
| 2019/0160051 A1 | 5/2019 | Arbeit et al. | |
| 2019/0322671 A1 | 10/2019 | Bourque et al. | |
| 2020/0123150 A1 | 4/2020 | Bourque et al. | |

FOREIGN PATENT DOCUMENTS

| | | |
|---|---|---|
| WO | WO-1999004794 | 2/1999 |
| WO | WO-1999031264 | 6/1999 |
| WO | WO-2000002870 | 1/2000 |
| WO | WO-2000022599 | 4/2000 |
| WO | WO-2000045814 | 8/2000 |
| WO | WO-2000056729 | 9/2000 |
| WO | WO-2002022600 | 3/2002 |
| WO | WO-2002034745 | 5/2002 |
| WO | WO-2002076948 | 10/2002 |
| WO | WO-2003011277 | 2/2003 |
| WO | WO-2003055876 | 7/2003 |
| WO | WO-2004019973 | 3/2004 |
| WO | WO-2004093817 | 11/2004 |
| WO | WO-2004106493 | 12/2004 |
| WO | WO-2006026703 | 3/2006 |
| WO | WO-2006036816 | 4/2006 |
| WO | WO-2006096444 | 9/2006 |
| WO | WO-2006138259 | 12/2006 |
| WO | WO-2007008539 | 1/2007 |
| WO | WO-2007027999 | 3/2007 |
| WO | WO-2007087548 | 8/2007 |
| WO | WO-2007087549 | 8/2007 |
| WO | WO-2009026251 | 2/2009 |
| WO | WO-2011147026 | 12/2011 |
| WO | WO-2012049277 | 4/2012 |
| WO | WO-2012075362 | 6/2012 |
| WO | WO-2012094703 | 7/2012 |
| WO | WO-2015030853 | 3/2015 |

(56) References Cited

FOREIGN PATENT DOCUMENTS

| WO | WO-2015038887 | 3/2015 |
|----|---------------|--------|
| WO | WO-2015069770 | 5/2015 |
| WO | WO-2015143012 | 9/2015 |
| WO | WO-2015200341 | 12/2015 |
| WO | WO-2016008976 | 1/2016 |
| WO | WO-2016146261 | 9/2016 |
| WO | WO-2016201425 | 12/2016 |
| WO | WO-2017048702 | 3/2017 |
| WO | WO-2017106328 | 6/2017 |
| WO | WO-2017106332 | 6/2017 |
| WO | WO-2017112894 | 6/2017 |
| WO | WO-2017127811 | 7/2017 |
| WO | WO-2017181073 | 10/2017 |
| WO | 2017223229 A1 | 12/2017 |
| WO | WO-2018237158 | 12/2018 |
| WO | 2019094392 A1 | 5/2019 |
| WO | 2019126106 A1 | 6/2019 |
| WO | 2019200223 A1 | 10/2019 |
| WO | 2020047410 A1 | 3/2020 |

OTHER PUBLICATIONS

"European Medicines Agency, Background Review for Sodium Laurilsulfate Used as an Excipient," Jul. 23, 2015, http://www.ema.europa.eu/docs/en_GB/document_library/Report/2015/08/WC500191475.pdf. p. 5, table 1. Date Accessed Jan. 23, 2017 (18 pages).

"Nivolumab," Drugbank, http://www.drugbank.ca/drugs/DB09035. Date Accessed, Nov. 30, 2018 (14 pages).

"Q3C—Tables and Lists, Guidance for Industry," U.S. Department of Health and Human Services, Food and Drug Adminstration, Center for Drug Evaluation and Research, Center for Biologics Evaluation and Research, Aug. 2018, https://www.fda.gov/downloads/Drugs/GuidanceComplianceRegulatoryInformation/Guidances/UCM073395.pdf. Date Accessed Jan. 22, 2019 (10 pages).

"Therapeutics," Encyclopedia Britannica Online, 2018, https://www.britannica.com/science/therapeutics. Date Accessed, Nov. 6, 2018 (1 page).

"WMA Declaration of Helsinki—Ethical Principles for Medical Research Involving Human Subjects," amended Oct. 2013, http://www.wma.net/en/30publications/10policies/b3/. Date Accessed Apr. 6, 2015 (4 Pages).

Abi-Younes et al., "The Stromal Cell-Derived Factor-1 Chemokine Is a Potent Platelet Agonist Highly Expressed in Atherosclerotic Plaques," Circulation Research, vol. 86, Feb. 4, 2000 (pp. 131-138).

Acharyya et al.,"CXCL1 paracrine network links cancer chemoresistance and metastasis." Cell, vol. 150, No. 1, 2012 (pp. 165-178).

Aduro Biotech, Inc., "Safety and Efficacy of MIW815 (ADU-S100)+/-Ipilimumab in Patients With Advanced/Metastatic Solid Tumors or Lymphomas," ClinicalTrials.gov: NCT02675439, First Posted: Feb. 5, 2016, Last Update: Sep. 26, 2018, https://clinicaltrials.gov/ct2/show/study/NCT02675439. Date Accessed, Mar. 18, 2019 (6 pages).

Aeglea Biotherapeutics, "A Multiple Dose, Dose Escalation Trial of AEB1102 in Patients With Advanced Solid Tumors," ClinicalTrials.gov: NCT02561234, First Posted: Sep. 28, 2015, Last Update: Mar. 22, 2019, https://clinicaltrials.gov/ct2/show/study/NCT02561234. Date Accessed, Mar. 25, 2019 (6 pages).

Aeglea Biotherapeutics, "A Multiple Dose, Dose Escalation Trial of AEB1102 in Patients With AML or MDS," ClinicalTrials.gov: NCT02732184, First Posted: Apr. 8, 2016, Last Update: Oct. 17, 2018, https://clinicaltrials.gov/ct2/show/study/NCT02732184. Date Accessed, Mar. 25, 2019 (6 pages).

Agenus Inc., "AGEN-1884, an Anti-CTLA-4 Antibody, in Advanced Solid Cancers," ClinicalTrials.gov: NCT02694822, First Posted: Mar. 1, 2016, Last Update: Jun. 27, 2017, https://clinicaltrials.gov/ct2/show/study/NCT02694822. Date Accessed, Mar. 25, 2019 (7 pages).

Aileron Therapeutics, "ALRN-6924 in Patients With Advanced Solid Tumors or Lymphomas," ClinicalTrials.gov: NCT02264613, First Posted: Oct. 15, 2014, Last Update: Jun. 27, 2017, https://clinicaltrials.gov/ct2/show/study/NCT02264613. Date Accessed, Mar. 25, 2019 (7 pages).

Aileron Therapeutics, "Safety Study of ALRN-6924 in Patients With Acute Myeloid Leukemia or Advanced Myelodysplastic Syndrome," ClinicalTrials.gov: NCT02909972, First Posted: Sep. 21, 2016, Last Update: Jun. 27, 2017, https://clinicaltrials.gov/ct2/show/study/NCT02909972. Date Accessed, Mar. 25, 2019 (7 pages).

ALX Oncology Inc., "A Study of ALX148 in Patients With Advanced Solid Tumors and Lymphoma," ClinicalTrials.gov: NCT03013218, First Posted: Jan. 6, 2017, Last Update: Aug. 8, 2018, https://clinicaltrials.gov/ct2/show/study/NCT03013218. Date Accessed, Mar. 18, 2019 (6 pages).

Ami and Horui, "Lipase-catalyzed Kinetic Resolution of (±)-trans and cis-2-Azidocycloalkanols," Bioscience, Biotechnology, Biochemistry, vol. 63, No. 12, 1999 (pp. 2150-2156).

An et al., "Solution phase combinatorial chemistry. Discovery of 13- and 15-membered polyazapyridinocyclophane libraries with antibacterial activity," Tetrahedron, vol. 54, (pp. 3999-4012).

Andtbacka et al., "X4P-001, an Orally Bioavailable CXCR4 Antagonist, Increases T Cell Infiltration in Human Metastatic Melanoma," The Society for Immunotherapy of Cancer Annual Meeting, National Harbor, Maryland, Nov. 8-12, 2017 (1 page).

AnorMed, "X4P-001 Product Page," Adis Insight, Published Online: Mar. 20, 2019, http://adisinsight.springer.com/drugs/800017499, Date Accessed, Apr. 1, 2019 (5 pages).

Arenburg et al., "The role of CXC chemokines in the regulation of angiogenesis in non-small cell lung cancer," Journal of Leukocyte Biology, vol. 62, 1997 (pp. 554-562).

Auiti et al., "The Chemokine SDF-1 Is a Chemoattractant for Human CD34+ Hematopoietic Progenitor Cells and Provides a New Mechanism to Explain the Mobilization of CD34+ Progenitors to Peripheral Blood," Journal of Experimental Medicine, vol. 185, No. 1, Jan. 6, 1997 (pp. 111-120).

Ayers et al., "IFN-γ-related mRNA profile predicts clinical response to PD-1 blockade," The Journal of Clinical Investigation, vol. 127, No. 8, 2017 (pp. 2930-2940).

Azilji et al., "New Developments in the Treatment of Metastatic Melanoma: Immune Checkpoint Inhibitors and Targeted Therapies," Anticancer Research, vol. 34, 2014 (pp. 1493-1506).

Baggiolini, "Chemokines and leukocyte traffic," Nature, vol. 392, Apr. 9, 1998 (pp. 565-568).

Balabanian, et al., "Proper desensitization of CXCR4 is required for lymphocyte development and peripheral compartmentalization in mice," Blood, vol. 119, No. 24, Mar. 2012 (pp. 5722-5730).

Balabanian, et al., "WHIM syndromes with different genetic anomalies are accounted for by impaired CXCR4 desensitization to CXCL12," Blood, vol. 105, No. 6, Mar. 15, 2005 (pp. 2449-2457).

Bayer, "Phase I Study of BAY1436032 in IDH1-mutant Advanced Solid Tumors," ClinicalTrials.gov: NCT02746081, First Posted: Apr. 21, 2016, Last Update: Mar. 19, 2019, https://clinicaltrials.gov/ct2/show/study/NCT02746081. Date Accessed, Mar. 25, 2019 (8 pages).

Beaussant-Cohen, et al., "Description and outcome of a cohort of 8 patients with WHIM syndrome from the French Severe Chronic Neutropenia Registry," Orphanet Journal of Rare Diseases, vol. 7, No. 71, Jun. 14, 2012 (pp. 5722-5730).

Berge et al., "Pharmaceutical Salts," Journal of Pharmaceutical Sciences, vol. 66, No. 1, Jan. 1977 (pp. 1-19).

Blaak et al., "In vivo HIV-1 infection of CD45RA+CD4+ T cells is established primarily by syncytium-inducing variants and correlates with the rate of CD4+ T cell decline," Proceedings of the National Academy of Sciences of the United States of America, vol. 97, No. 3, 2000 (pp. 1269-1274).

Blanchette, S., "NCT02823405: X4P-001 and Prembrolizumab in Patents With Advanced Melanoma (X4P-001-MELA)," Jul. 6, 2016, https://clinicaltrials.gov/ct2/show/NCT02823405> Date Accessed Oct. 5, 2018 (7 pages).

Blanco et al. "The CXCR4 Antagonist AMD3100 Efficiently Inhibits Cell-Surface-Expressed Human Immunodeficiency Virus Type 1

(56) References Cited

OTHER PUBLICATIONS

Envelope-Induced Apoptosis," Antimicrobial Agents and Chemotherapy, vol. 44, No. 1., Jan. 2000 (pp. 51-56).
Bleul et al., "B Lymphocyte Chemotaxis Regulated in Association with Microanatomic Localization, Differentiation State, and B Cell Receptor Engagement," Journal of Experimental Medicine, vol. 187, No. 5, Mar. 2, 1998 (pp. 753-762).
Bohinjec, "Myelokathexis: chronic neutropenia with hyperplastic bone marrow and hypersegmented neutrophils in two siblings," Blut, vol. 42, 1981 (pp. 191-196).
Boutsikou et al., "Tumour necrosis factor, interferon-gamma and interleukins as predictive markers of antiprogrammed cell-death protein-1 treatment in advanced non-small cell lung cancer: a pragmatic approach in clinical practice," Therapeutic Advances in Medical Oncology, vol. 10, 2018 (pp. 1-8).
Bristol-Myers Squibb, "A Phase I Open Label Study of the Safety and Tolerability of Elotuzumab (BMS-901608) Administered in Combination With Either Lirilumab (BMS-986015) or Urelumab (BMS-663513) in Subjects With Multiple Myeloma," ClinicalTrials.gov: NCT02252263, First Posted: Sep. 30, 2014, Last Update: Nov. 1, 2017, https://clinicaltrials.gov/ct2/show/study/NCT02252263. Date Accessed, Mar. 18, 2019 (7 pages).
Bristol-Myers Squibb, "An Investigational Immuno-therapy Study of Experimental Medication BMS-986178 by Itself or in Combination With Nivolumab and/or Ipilimumab in Patients With Solid Cancers That Are Advanced or Have Spread," ClinicalTrials.gov: NCT02737475, First Posted: Apr. 14, 2016, Last Update: Jan. 31, 2019, https://clinicaltrials.gov/ct2/show/study/NCT02737475. Date Accessed, Mar. 18, 2019 (11 pages).
Bristol-Myers Squibb, "An Investigational Immuno-therapy Study of Experimental Medication BMS-986179 Given Alone and in Combination With Nivolumab," ClinicalTrials.gov: NCT02754141, First Posted: Apr. 28, 2016, Last Update: Feb. 1, 2019, https://clinicaltrials.gov/ct2/show/study/NCT02754141. Date Accessed, Mar. 18, 2019 (8 pages).
Bristol-Myers Squibb, "An Investigational Immuno-Therapy Study to Determine the Safety and Effectiveness of Nivolumab and Daratumumab in Patients With Multiple Myeloma," ClinicalTrials.gov: NCT01592370, First Posted: May 7, 2012, Last Update: Jan. 15, 2019, https://clinicaltrials.gov/ct2/show/study/NCT01592370. Date Accessed, Mar. 18, 2019 (9 pages).
Bristol-Myers Squibb, "An Investigational Immuno-therapy Study to Evaluate the Safety and Effectiveness of Experimental Medication BMS-986207 by Itself and in Combination With Nivolumab in Solid Cancers That Are Advanced or Have Spread," ClinicalTrials.gov: NCT02913313, First Posted: Sep. 23, 2016, Last Update: Jan. 31, 2019, https://clinicaltrials.gov/ct2/show/study/NCT02913313. Date Accessed, Mar. 25, 2019 (9 pages).
Bristol-Myers Squibb, "An Investigational Immuno-therapy Study to Investigate the Safety and Effectiveness of Nivolumab, and Nivolumab Combination Therapy in Virus-associated Tumors (CheckMate358)," ClinicalTrials.gov: NCT02488759, First Posted: Jul. 2, 2015, Last Update: Oct. 19, 2018, https://clinicaltrials.gov/ct2/show/study/NCT02488759. Date Accessed Nov. 29, 2018 (7 pages).
Bristol-Myers Squibb, "Safety and Efficacy Study of Ulocuplumab and Nivolumab in Subjects With Solid Tumors (CXCessoR4)," ClinicalTrials.gov: NCT02472977, First Posted: Jun. 16, 2015, Last Update: Nov. 1, 2018, https://clinicaltrials.gov/ct2/show/study/NCT02472977. Date Accessed, Aug. 20, 2019 (7 pages).
Broxmeyer et al., "Effects of in vivo treatment with PIXY321 (GM-CSF/IL-3 fusion protein) on proliferation kinetics of bone marrow and blood myeloid progenitor cells in patients with sarcoma," Experimental Hematology, vol. 23, 1995 (pp. 335-340).
Broxmeyer, "A WHIM satisfactorily addressed," Blood, vol. 123, No. 15, 2014 (pp. 2286-2288).
Burger et al., "Chronic Lymphocytic Leukemia B Cells Express Functional CXCR4 Chemokine Receptors That Mediate Spontaneous Migration Beneath Bone Marrow Stromal Cells," Blood, vol. 94, No. 11, Dec. 1, 1999 (pp. 3658-3667).

Canadian Cancer Trials Group, "Reolysin Combined With Docetaxel and Prednisone or Docetaxel and Prednisone Alone in Metastatic Castration Resistant Prostate Cancer," ClinicalTrials.gov: NCT01619813, First Posted: Jun. 14, 2012, Last Update: Jan. 23, 2019, https://clinicaltrials.gov/ct2/show/study/NCT01619813. Date Accessed, Mar. 25, 2019 (8 pages).
Canadian Cancer Trials Group, "Reolysin in Combination With FOLFOX6 and Bevacizumab or FOLFOX6 and Bevacizumab Alone in Metastatic Colorectal Cancer," ClinicalTrials.gov: NCT01622543 First Posted: Jun. 19, 2012, Last Update: Feb. 1, 2018, https://clinicaltrials.gov/ct2/show/study/NCT01622543. Date Accessed, Mar. 25, 2019 (8 pages).
Cao, et al., "Effect of Low-Dose Ritonavir on the Pharmacokinetics of the CXCR4 Antagonist AMD070 in Healthy Volunteers," Antimicrobial Agents and Chemotherpy, vol. 52, No. 5, 2008 (pp. 1630-1634).
Catalano, J. G. et al., "Synthesis of a novel tricyclic 1, 2,3,4, 4a, 5,, 10b-octahydro-1, 10-phenanthroline ring system and CXCR4 antagonists with potent activity against HIV-1," Bioorganic & Medicinal Chemistry Letters, vol. 20, 2010 (pp. 2186-2190).
Celgene, "A Safety and Efficacy Study of Oral AG-120 Plus Subcutaneous Azacitidine and Oral AG-221 Plus Subcutaneous Azacitidine in Subjects With Newly Diagnosed Acute Myeloid Leukemia (AML)," ClinicalTrials.gov: NCT02677922, First Posted: Feb. 9, 2016, Last Update: Feb. 21, 2019, https://clinicaltrials.gov/ct2/show/study/NCT02677922. Date Accessed, Mar. 20, 2019 (11 pages).
Celgene, "A Study of CC-90002 in Subjects With Acute Myeloid Leukemia (AML) and High-risk Myelodysplastic Syndrome (MDS)," ClinicalTrials.gov: NCT02641002, First Posted: Dec. 29, 2015, Last Update: Oct. 18, 2018, https://clinicaltrials.gov/ct2/show/study/NCT02641002. Date Accessed, Mar. 18, 2019 (7 pages).
Celgene, "An Efficacy and Safety Study of AG-221 (CC-90007) Versus Conventional Care Regimens in Older Subjects With Late Stage Acute Myeloid Leukemia Harboring an Isocitrate Dehydrogenase 2 Mutation (IDHENTIFY)," ClinicalTrials.gov: NCT02577406, First Posted: Oct. 16, 2015, Last Update: Feb. 21, 2019, https://clinicaltrials.gov/ct2/show/study/NCT02577406. Date Accessed, Mar. 25, 2019 (12 pages).
Celldex Therapeutics, "A Dose Escalation and Cohort Expansion Study of Anti-CD27 (Varlilumab) and Anti-PD-1 (Nivolumab) in Advanced Refractory Solid Tumors," ClinicalTrials.gov: NCT02335918, First Posted: Jan. 12, 2015, Last Update: Jan. 7, 2019, https://clinicaltrials.gov/ct2/show/study/NCT02335918. Date Accessed, Mar. 18, 2019 (9 pages).
Celldex Therapeutics, "A Study of CDX-1127 (Varlilumab) in Patients With Select Solid Tumor Types or Hematologic Cancers," ClinicalTrials.gov: NCT01460134, First Posted: Oct. 26, 2011, Last Update: Jan. 31, 2018, https://clinicaltrials.gov/ct2/show/study/NCT01460134. Date Accessed, Mar. 18, 2019 (9 pages).
Centre Leon Berard, "Evaluation of Safety and Activity of an Anti-PDL1 Antibody (Durvalumab) Combined With CSF-1R TKI (Pexidartinib) in Patients With Metastatic/Advanced Pancreatic or Colorectal Cancers (Mediplex)," ClinicalTrials.gov: NCT02777710, First Posted: May 19, 2016, Last Update: Jan. 17, 2019, https://clinicaltrials.gov/ct2/show/study/NCT02777710. Date Accessed, Mar. 18, 2019 (10 pages).
Chen et al., "CXCR4 inhibition in tumor microenvironmental facilitates anti-programmed death receptor-1 immunotherapy in sorafenib-treated hepatocellular carcinoma in mice," Hepatology, vol. 61, No. 5, May 2015, (pp. 1591-1602).
Clark, PE., "Rationale for targeted therapies and potential role of pazopanib in advanced renal cell carcinoma," Biologies: Targets and Therapy, vol. 4, Jun. 26, 2010 (pp. 187-197).
Cold Genesys, Inc., "Safety and Efficacy of CG0070 Oncolytic Virus Regimen for High Grade NMIBC After BCG Failure (BOND2)," ClinicalTrials.gov: NCT02365818, First Posted: Feb. 19, 2015, Last Update: Mar. 20, 2019, https://clinicaltrials.gov/ct2/show/study/NCT02365818. Date Accessed, Mar. 25, 2019 (9 pages).
Comba et al., "Catalytic Aziridination of Styrene with Copper Complexes for Substituted 3,7-Diazabicyclo[3.3.1]nonanones," European Journal of Inorganic Chemistry, vol. 9, 2003 (pp. 1711-1718).

(56) References Cited

OTHER PUBLICATIONS

Connolly et al., "Complexities of TGF-β Targeted Cancer Therapy," (2012) International Journal of Biological Sciences vol. 8, No. 7, Jul. 2012 (pp. 964-978).
Connor et al., "Human Immunodeficiency Virus Type 1 Variants with Increased Replicative Capacity Develop during the Asymptomatic Stage before Disease Progression," Journal of Virology, vol. 68, No. 7, 1994 (pp. 4400-4408).
Courtney et al., "Optimizing recent advances in metastatic renal cell carincoma," Current Onocology Reports, vol. 11, No. 3, May 1, 2009 (pp. 218-226).
Crawford et al., "AMD070, a CXCR4 Chemokine Receptor Antagonist: Practical Large-Scale Laboratory Synthesis," Organic Process Research and Development, vol. 12, No. 5, 2008 (pp. 823-830).
Crump et al., "Solution structure and basis for functional activity of stromal cell derived factor-1; dissociation of CXCR4 activation from binding and inhibition of HIV-1," The EMBO Journal, vol. 16, No. 23, 1997 (pp. 6996-7007).
D'Alterio, et al., "Inhibition of stromal CXCR4 impairs development of lung metastases," Cancer Immunology, Immunotherapy, vol. 61, 2012 (pp. 1713-1720).
Dale et al., "Effects of Granulocyte-Macrophage Colony-Stimulating Factor (GM-CSF) on Neutrophil Kinetics and Function in Normal Human Volunteers," American Journal of Hematology, (1998), vol. 57, 1998 (pp. 7-15).
Dale et al., "The CXCR4 antagonist plerixafor is a potential therapy for myelokathexis, WHIM syndrome," Blood, vol. 118, No. 18, Nov. 3, 2011 (pp. 4963-4966).
Dale et al., "The Severe Chronic Neutropenia International Registry: 10-Year Follow-up Report," Supportive Cancer Therapy, vol. 3, No. 4, 2006 (pp. 220-231).
Dana-Farber Cancer Institute, "LY3022855 With BRAF/MEK Inhibition in Patients With Melanoma," ClinicalTrials.gov: NCT03101254, First Posted: Apr. 5, 2017, Last Update: Feb. 4, 2019, https://clinicaltrials.gov/ct2/show/study/NCT03101254. Date Accessed, Mar. 18, 2019 (9 pages).
Debnath et al., "Small molecule inhibitors of CXCR4," Theranostics, vol. 3, No. 1, Jan. 15, 2013 (pp. 47-75).
DePrimo et al., "Circulating protein biomarkers of pharmacodynamic activity of sunitinib in patients with metastatic renal cell carcinoma: modulation of VEGF and VEGF-related proteins," Journal of Translational Medicine, vol. 5, No. 32, Jul. 2, 2007 (11 pages).
Doranz, "Chemokine receptors as fusion cofactors for human immunodeficiency virus type 1 (HIV-1)," Immunologic Research, vol. 16, 1997 (pp. 15-28).
Dorwald, "Side Reactions in Organic Synthesis," Wiley: VCH, Weinheim, 2005 (p. IX of preface and pp. 1-15, 41).
Doha et al., "Clinical and genetic features of warts, hypogammaglobulinemia, infections and myelokathexis (WHIM) syndrome," Current Molecular Medicine, vol. 11, 2011 (pp. 317-325).
Duda et al., "CXCL12 (SDF1a)-CXCR4/CXCR7 Pathway Inhibition: An Emerging Sensitizer for Anticancer Therapies?," Clinical Cancer Research, vol. 17, No. 8, 2011 (pp. 2074-2080).
Egberink et al., "Bicyclams, Selective Antagonists of the Human Chemokine Receptor CXCR4, Potently Inhibit Feline Immunodeficiency Virus Replication," Journal of Virology, vol. 73, No. 8, 1999 (pp. 6346-6352).
Eli Lilly and Company, "A Study of LY3022855 in Combination With Durvalumab or Tremelimumab in Participants With Advanced Solid Tumors," ClinicalTrials.gov: NCT02718911, First Posted: Mar. 24, 2016, Last Update: Jan. 15, 2019, https://clinicaltrials.gov/ct2/show/study/NCT02718911. Date Accessed, Mar. 18, 2019 (7 pages).
Eli Lilly and Company, "A Study of LY3321367 Alone or With LY3300054 in Participants With Advanced Relapsed/Refractory Solid Tumors," ClinicalTrials.gov: NCT03099109, First Posted: Apr. 4, 2017, Last Update: Mar. 5, 2019, https://clinicaltrials.gov/ct2/show/study/NCT03099109. Date Accessed, Mar. 25, 2019 (10 pages).

EMD Serono Research & Development Institute, Inc., "MSB0011359C (M7824) in Metastatic or Locally Advanced Solid Tumors," ClinicalTrials.gov: NCT02517398, First Posted: Aug. 7, 2015, Last Update: Nov. 19, 2018, https://clinicaltrials.gov/ct2/show/study/NCT02517398. Date Accessed, Mar. 25, 2019 (8 pages).
Facciabene et al., "Tumour hypoxia promotes tolerance and angiogenesis via CCL28 and Treg cells," Nature, vol. 475, 2011 (pp. 226-230).
Fedyk et al., "Maturation decreases responsiveness of human bone marrow B lineage cells to stromal-derived factor 1 (SDF-1)," Journal of Leukocyte Biology, vol. 66, Oct. 1999 (pp. 667-673).
Feig et al., "Targeting CXCL12 from FAP-expressing carcinoma-associated fibroblasts synergizes with anti-PD-L1 immunotherapy in pancreatic cancer," PNAS, vol. 110, No. 50, 2013 (p. 20212-20217).
Finke J. et al., "MDSC as a mechanism of tumor escape from sunitinib mediated anti-angiogenic therapy," International Immunopharmacology, vol. 11, No. 7, Jul. 2011 (pp. 856-861).
Forty Seven, Inc., "CAMELLIA: Anti-CD47 Antibody Therapy in Haematological Malignancies," ClinicalTrials.gov: NCT02678338, First Posted: Feb. 9, 2016, Last Update: Feb. 21, 2019, https://clinicaltrials.gov/ct2/show/study/NCT02678338. Date Accessed, Mar. 18, 2019 (5 pages).
Forty Seven, Inc., "Trial of Hu5F9-G4 in Combination With Cetuximab in Patients With Solid Tumors and Advanced Colorectal Cancer," ClinicalTrials.gov: NCT02953782, First Posted: Nov. 3, 2016, Last Update: Aug. 1, 2018, https://clinicaltrials.gov/ct2/show/study/NCT02953782. Date Accessed, Mar. 18, 2019 (7 pages).
Forty Seven, Inc., "Trial of Hu5F9-G4 in Combination With Rituximab in Relapsed/Refractory B-cell Non-Hodgkin's Lymphoma," ClinicalTrials.gov: NCT02953509, First Posted: Nov. 2, 2016, Last Update: Feb. 8, 2019, https://clinicaltrials.gov/ct2/show/study/NCT02953509. Date Accessed, Mar. 18, 2019 (8 pages).
Gacche, RN. "Compensatory angiogenesis and tumor refractoriness," Oncogenesis, vol. 4, e153, Jun. 1, 2015 (8 pages).
Gale et al., "Chemokines: extracellular messengers for all occasions?," BioEssays, vol. 21, 1999 (pp. 17-28).
Galsky et al., "A Phase I Trial of LY2510924, a CXCR4 Peptide Antagonist, in Patients with Advanced Cancer," Clinical Cancer Research, vol. 20, No. 16, Aug. 15, 2014 (pp. 3581-3588; 4414).
Genelux Corporation, "GL-ONC1 Oncolytic Immunotherapy in Patients With Recurrent or Refractory Ovarian Cancer," ClinicalTrials.gov: NCT02759588, First Posted: May 3, 2016, Last Update: Nov. 8, 2018, https://clinicaltrials.gov/ct2/show/study/NCT02759588. Date Accessed, Mar. 25, 2019 (8 pages).
Genelux GmbH, "A Study of GL-ONC1, an Oncolytic Vaccinia Virus, in Patients With Advanced Peritoneal Carcinomatosis," ClinicalTrials.gov: NCT01443260, First Posted: Sep. 29, 2011, Last Update: Mar. 10, 2015, https://clinicaltrials.gov/ct2/show/study/NCT01443260. Date Accessed, Mar. 25, 2019 (6 pages).
Genzyme, a Sanofi Company, "Safety and Efficacy Study of GC1008 to Treat Renal Cell Carcinoma or Malignant Melanoma," ClinicalTrials.gov: NCT00356460, First Posted: Jul. 26, 2006, Last Update: Mar. 19, 2014, https://clinicaltrials.gov/ct2/show/study/NCT00356460. Date Accessed, Mar. 25, 2019 (10 pages).
Glaspy et al., "Peripheral Blood Progenitor Cell Mobilization Using Stem Cell Factor in Combination With Filgrastim in Breast Cancer Patients," Blood, vol. 90, 1997 (pp. 2939-2951).
GlaxoSmithKline, "Dose Escalation and Expansion Study of GSK3359609 in Subjects With Selected Advanced Solid Tumors (INDUCE-1)," ClinicalTrials.gov: NCT02723955, First Posted: Mar. 31, 2016, Last Update: Feb. 25, 2019, https://clinicaltrials.gov/ct2/show/study/NCT02723955. Date Accessed, Mar. 18, 2019 (25 pages).
GlaxoSmithKline, "GSK3174998 Alone or With Pembrolizumab in Subjects With Advanced Solid Tumors (ENGAGE-1)," ClinicalTrials.gov: NCT02528357, First Posted: Aug. 19, 2015, Last Update: Jun. 1, 2018, https://clinicaltrials.gov/ct2/show/study/NCT02528357. Date Accessed, Mar. 18, 2019 (11 pages).
Gonzalo et al., "Critical Involvement of the Chemotactic Axis CXCR4/Stromal Cell-Derived Factor-1α in the Inflammatory Component of Allergic Airway Disease," Journal of Immunology, vol. 165, No. 1, Jul. 1, 2000 (pp. 499-508).
Gudmundsson, K.S., "Amine sustituted N-(1H-benzimidazol-2ylmethyl)-5,6,7,8-tetrahydro-8-quino-linamines as CXCR4 antago-

(56) References Cited

OTHER PUBLICATIONS nists with potent activity against HIV-1," Bioorganic & Medicinal Chemistry Letters, 2009 (pp. 1-5).
Gulino et al., "Altered leukocyte response to CXCL12 in patients with warts hypogammaglobulinemia, infections, myelokathexis (WHIM) syndrome," Blood, vol. 104, No. 2, 2014 (pp. 444-452).
H. Lee Moffitt Cancer Center and Research Institute, "Combining PD-1 Blockade, CD137 Agonism and Adoptive Cell Therapy for Metastatic Melanoma," ClinicalTrials.gov: NCT02652455, First Posted: Jan. 11, 2016, Last Update: Dec. 4, 2018, https://clinicaltrials.gov/ct2/show/study/NCT02652455. Date Accessed, Mar. 18, 2019 (9 pages).
Hamid et al., "Safety and Tumor Responses with Lambrolizumab (Anti-PD-1) in Melanoma," New England Journal of Medicine, vol. 369, No. 2, 2013 (pp. 134-144).
Hendrix et al., "Pharmacokinetics and safety of AMD-3100, a novel antagonist of the CXCR-4 chemokine receptor, in human volunteers," Antimicrobial Agents and Chemotherapy, vol. 44, No. 6, Jun. 2000 (pp. 1667-1673).
Hendrix, et al., "Safety, Pharmacokinetics, and Antiviral Activity of AMD3100, a Selective CXCR4 Receptor Inhibitor, in HIV-1 Infection," Journal of Acquired Immune Deficiency Syndrome, vol. 37, No. 2. Oct. 1, 2004 (pp. 1253-1262).
Hernandez et al., "Mutations in the chemokine receptor gene CXCR4 are associated with WHIM syndrome, a combined immunodeficiency disease," Nature Genetics, vol. 34, No. 1., May 31, 2003 (pp. 70-74).
Hesselgesser et al., "CD-4-independent association between HIV-1 gp120 and CXCR4: functional chemokine receptors are expressed in human neurons," Current Biology, vol. 7, No. 2, Jan. 21, 1997 (pp. 112-121).
Hesselgesser et al., "Neuronal apoptosis inducted by HIV-1 gp120 and chemokine SDF-1α is mediated by the chemokine receptor CXCR4," Current Biology, vol. 8, No. 10, Apr. 27, 1998 (pp. 595-598).
Highfill et al., "Disruption of CXCR2-mediated MDSC tumor trafficking enhances anti-PD1 efficacy," Science Translational Medicine, vol. 6, No. 237, May 21, 2014 (pp. 1-13).
Husain Z. et al., "Tumor-derived lactate modifies antitumor immune response: Effect on myeloid-derived suppressor cells and NK cells," Journal of Immunology, vol. 191, 2013 (pp. 1486-1495).
Immutep Australia Pty. Ltd., "Phase 1 Study of IMP321 (Eftilagimod Alpha) Adjuvant to Anti-PD-1 Therapy in Unresectable or Metastatic Melanoma (TACTI-mel)," ClinicalTrials.gov: NCT02676869, First Posted: Feb. 8, 2016, Last Update: Jan. 11, 2019, https://clinicaltrials.gov/ct2/show/study/NCT02676869. Date Accessed, Mar. 25, 2019 (6 pages).
Immutep S.A., "IMP321 (Eftilagimod Alpha) as Adjunctive to a Standard Chemotherapy Paclitaxel Metastatic Breast Carcinoma," ClinicalTrials.gov: NCT02614833, First Posted: Nov. 25, 2015, Last Update: Mar. 18, 2019, https://clinicaltrials.gov/ct2/show/study/NCT02614833. Date Accessed, Mar. 25, 2019 (9 pages).
Immutep S.A., "IMP321 Plus First-line Paclitaxel in Metastatic Breast Carcinoma," ClinicalTrials.gov: NCT00349934, First Posted: Jul. 10, 2006, Last Update: Jan. 7, 2010, https://clinicaltrials.gov/ct2/show/study/NCT00349934. Date Accessed, Mar. 25, 2019 (7 pages).
Incyte Biosciences International Sàrl, "An Open-Label, Dose-Escalation, Safety Study of INCAGN01876 in Subjects With Advanced or Metastatic Solid Tumors," ClinicalTrials.gov: NCT02697591, First Posted: Mar. 3, 2016, Last Update: Oct. 31, 2018, https://clinicaltrials.gov/ct2/show/study/NCT02697591. Date Accessed, Mar. 18, 2019 (6 pages).
Incyte Biosciences International Sàrl, "Phase 1/2 Study Exploring the Safety, Tolerability, and Efficacy of INCAGN01876 Combined With Immune Therapies in Advanced or Metastatic Malignancies," ClinicalTrials.gov: NCT03126110, First Posted: Apr. 24, 2017, Last Update: Dec. 10, 2018, https://clinicaltrials.gov/ct2/show/study/NCT03126110. Date Accessed, Mar. 18, 2019 (7 pages).

Innate Pharma, "Combination Study of IPH2201 With Ibrutinib in Patients With Relapsed, Refractory or Previously Untreated Chronic Lymphocytic Leukemia," ClinicalTrials.gov: NCT02557516, First Posted: Sep. 23, 2015, Last Update: Apr. 24, 2018, https://clinicaltrials.gov/ct2/show/study/NCT02557516. Date Accessed, Mar. 20, 2019 (6 pages).
Innate Pharma, "Efficacy Study of Anti-KIR Monoclonal Antibody as Maintenance Treatment in Acute Myeloid Leukemia (EFFIKIR) (EFFIKIR)," ClinicalTrials.gov: NCT01687387, First Posted: Sep. 18, 2012, Last Update: Feb. 8, 2019, https://clinicaltrials.gov/ct2/show/study/NCT01687387. Date Accessed, Mar. 18, 2019 (9 pages).
Innate Pharma, "Study of IPH4102 in Patients With Relapsed/Refractory Cutaneous T-cell Lymphomas (CTCL)," ClinicalTrials.gov: NCT02593045, First Posted: Oct. 30, 2015, Last Update: Feb. 12, 2019, https://clinicaltrials.gov/ct2/show/study/NCT02593045. Date Accessed, Mar. 18, 2019 (6 pages).
Innate Pharma, "Study of Monalizumab and Cetuximab in Patients With Recurrent or Metastatic Squamous Cell Carcinoma of the Head and Neck," ClinicalTrials.gov: NCT02643550, First Posted: Dec. 31, 2015, Last Update: Sep. 13, 2018, https://clinicaltrials.gov/ct2/show/study/NCT02643550. Date Accessed, Mar. 20, 2019 (9 pages).
Innate Pharma, "Study on the Anti-tumor Activity, Safety and Pharmacology of IPH2101 in Patients With Smoldering Multiple Myeloma (KIRMONO)," ClinicalTrials.gov: NCT01222286, First Posted: Oct. 18, 2010, Last Update: May 9, 2014, https://clinicaltrials.gov/ct2/show/study/NCT01222286. Date Accessed, Mar. 18, 2019 (7 pages).
Innate Pharma, "Study on the Safety, Anti-tumor Activity and Pharmacology of IPH2101 Combined With Lenalidomide in Patients With Multiple Myeloma Experiencing a First or Second Relapse (KIRIMID)," ClinicalTrials.gov: NCT01217203, First Posted: Oct. 8, 2010, Last Update: Feb. 28, 2014, https://clinicaltrials.gov/ct2/show/study/NCT01217203. Date Accessed, Mar. 18, 2019 (7 pages).
International Preliminary Examination Report for PCT/US2002/041407, titled "Chemokine Receptor Binding Heterocyclic Compounds with Enhanced Efficacy," dated Aug. 1, 2003 (4 pages).
International Preliminary Report on Patentability for PCT/US2004/015977, titled "Chemokine Receptor Binding Heterocyclic Compounds with Enhanced Efficacy," dated May 2, 2006 (4 pages).
International Search Report and Written Opinion issued by the United States Patent and Trademark Office as International Searching Authority for International Patent Application No. PCT/US2016/066634, dated Feb. 16, 2017 (15 pages).
International Search Report and Written Opinion issued by the United States Patent and Trademark Office as International Searching Authority for International Patent Application No. PCT/US2016/066639, dated Feb. 16, 2017 (11 pages).
International Search Report and Written Opinion issued by the United States Patent and Trademark Office as International Searching Authority for International Patent Application No. PCT/US2016/068394, dated Mar. 3, 2017 (10 pages).
International Search Report and Written Opinion issued by the United States Patent and Trademark Office as International Searching Authority for International Patent Application No. PCT/US2017/014578, dated Apr. 4, 2017 (12 pages).
International Search Report and Written Opinion issued by the United States Patent and Trademark Office as International Searching Authority for International Patent Application No. PCT/US2018/066141, dated Mar. 8, 2019 (8 pages).
International Search Report issued by the United States Patent and Trademark Office as International Searching Authority for International Patent Application No. PCT/US05/34491, dated Apr. 11, 2006 (2 pages).
International Search Report issued by the United States Patent and Trademark Office as International Searching Authority for International Patent Application No. PCT/US05/34950, dated Oct. 4, 2006 (4 pages).
International Search Report issued by the United States Patent and Trademark Office as International Searching Authority for International Patent Application No. PCT/US2002/029372, dated Aug. 10, 2004 (4 pages).

(56) References Cited

OTHER PUBLICATIONS

International Search Report issued by the United States Patent and Trademark Office as International Searching Authority for International Patent Application No. PCT/US2004/011328, dated Oct. 20, 2004 (2 pages).
International Search Report issued by the United States Patent and Trademark Office as International Searching Authority for International Patent Application No. PCT/US2004/012627, dated Jan. 13, 2005 (3 pages).
International Search Report issued by the United States Patent and Trademark Office as International Searching Authority for International Patent Application No. PCT/US2004/015977, dated Jul. 15, 2005 (3 pages).
International Search Report issued by the United States Patent and Trademark Office as International Searching Authority for International Patent Application No. PCT/US2005/08268, dated May 26, 2005 (3 pages).
Ishii et al., "Expression of Stromal Cell-Derived Factor-1/Pre-B Cell Growth-Stimulating Factor Receptor, CXC Chemokine Receptor 4, on CD34+ Human Bone Marrow Cells Is a Phenotypic Alteration for Committed Lymphoid Progenitors," The Journal of Immunology, vol. 163, 1999 (pp. 3612-3620).
Iwakura et al., "AMD-3100, a CXCR4 Antagonist, Augments Incorporation of Bone Marrow-Derived Eendothelial Progenitor Cells into Sites of Myocardial Neovascularization," Abstract # 1127, Poster Board #-Session: 2931, Blood, vol. 100, No. 11, Nov. 16, 2002 (pp. 293A-294A).
Jackson et al., "Regeneration of ischemic cardiac muscle and vascular endothelium by adult stem cells," The Journal of Clinical Investigation, vol. 107, No. 1, Jun. 2011 (pp. 1395-1402).
Jennerex Biotherapeutics, "A Study of Recombinant Vaccinia Virus to Treat Malignant Melanoma," ClinicalTrials.gov: NCT00429312, First Posted: Jan. 31, 2007, Last Update: Jan. 15, 2015, https://clinicaltrials.gov/ct2/show/study/NCT00429312. Date Accessed, Mar. 25, 2019 (7 pages).
Jounce Therapeutics, Inc., "JTX-2011 Alone and in Combination With Anti-PD-1 or Anti-CTLA-4 in Subjects With Advanced and/or Refractory Solid Tumors (ICONIC)," ClinicalTrials.gov: NCT02904226, First Posted: Sep. 16, 2016, Last Update: Jun. 28, 2018, https://clinicaltrials.gov/ct2/show/study/NCT02904226. Date Accessed, Mar. 18, 2019 (11 pages).
Kawai et al., "Enhanced function with decreased internalization of carboxy-terminus truncated CXCR4 responsible for WHIM syndrome," Experimental Hematology, vol. 33, 2005 (pp. 460-468).
Kawai et al., "WHIM syndrome myelokathexis reproduced in the NOD/SCID mouse xenotransplant model engrafted with healthy human stem cells transduced with C-terminus-truncated CXCR4," Blood, vol. 109, No. 1, Jan. 1, 2007 (pp. 78-84), Epub Aug. 31, 2006.
Kawai et al., "WHIM syndrome: congenital immune deficiency disease," Current Opinion in Hematology, vol. 16, No. 1, Jan. 2009 (pp. 20-26).
Kim, et al., "CXCR4 signaling regulates metastasis of chemoresistant melanoma cells by a lymphatic metastatic niche," Cancer Research, vol. 70, No. 24, 2010 (pp. 10411-10421).
King, A. G. et al. "Rapid Mobilization of Murine Hematopoietic Stem Cells With Enhanced Engraftment Properties and Evaluation of Hematopoietic Progenitor Cell Mobilization in Rhesus Monkeys by a Single Injection of SB-251353, a Specific Truncated Form of the Human CXC Chemokine GROI3," Blood, vol. 97, No. 6, 2001 (pp. 1534-1542).
Kirkland et al., "Quantitation of Mafosfamide-Resistant Pre-Colony-Forming Units in Allogeneic Bone Marrow Transplantation: Relationship With Rate of Engraftment and Evidence for Long-Lasting Reduction in Stem Cell Numbers," Blood, vol. 87, No. 9, 1996 (pp. 3963-3969).
Kocher et al. "Neovascularization of ischemic myocardium by human bone-marrow-derived angioblasts prevents cardiomyocyte apoptosis, reduces remodeling and improves cardiac function," Nature Medicine, vol. 7, 2001 (pp. 430-436).

Lagane et al., "CXCR4 dimerization and beta-arrestin-mediated signaling account for the enhanced chemotaxis to CXCL12 in WHIM syndrome," Blood, vol. 112, No. 1, Jul. 1, 2008 (pp. 34-44).
Langan et al., "Liver Directed Therapy for Renal Cell Carcinoma," Journal of Cancer, vol. 3, 2012 (pp. 184-190).
Lapidot et al., "Current understanding of stem cell mobilization: the roles of chemokines, proteolytic enzymes, adhesion molecules, cytokines, and stromal cells," Experimental Hematology, vol. 30, 2002, (pp. 973-981).
Lapidot et al., "The essential roles of the chemokine SDF-1 and its receptor CXCR4 in human stem cell homing and repopulation of transplanted immune-deficient NOD/SCID and NOD/SCID/B2m(null) mice," Leukemia, vol. 16, 2002 (pp. 1992-2003).
Lataillade et al., "Chemokine SDF-1 enhances circulating CD341 cell proliferation in synergy with cytokines: possible role in progenitor survival," Blood, vol. 95, No. 3., 1999 (pp. 756-768).
Leap Therapeutics, Inc., "Phase 1 Open-label Study of TRX518 Monotherapy and TRX518 in Combination With Gemcitabine, Pembrolizumab, or Nivolumab," ClinicalTrials.gov: NCT02628574, First Posted: Dec. 11, 2015, Last Update: Jan. 17, 2018, https://clinicaltrials.gov/ct2/show/study/NCT02628574. Date Accessed, Mar. 18, 2019 (8 pages).
Leap Therapeutics, Inc., "Trial of TRX518 (Anti-GITR mAb) in Stage III or IV Malignant Melanoma or Other Solid Tumors (TRX518-001)," ClinicalTrials.gov: NCT01239134, First Posted: Nov. 11, 2010, Last Update: Aug. 14, 2018, https://clinicaltrials.gov/ct2/show/study/NCT01239134. Date Accessed, Mar. 18, 2019 (8 pages).
Lee et al., "Coreceptor/Chemokine Receptor Expression on Human Hematopoietic Cells: Biological Implications for Human Immunodeficiency Virus-Type 1 Infection," Blood, vol. 93, No. 4, 1999 (pp. 1145-1156).
Liu et al., "Homozygous defect in HIV-1 coreceptor accounts for resistance of some multiply-exposed individuals to HIV-1 infection," Cell, vol. 86, No. 3, 1996 (pp. 367-377).
Lord, B. I. et al "Mobilization of Early Hematopoietic Progenitor Cells with BB-1001-: A Genetically Engineered Variant of Human Macrophage Inflammatory Protein-1 alpha," Blood, vol. 85, No. 12, 1995 (pp. 3412-3415).
Ludwig Institute for Cancer Research, "A Phase 1/2 Study of Motolimod (VTX-2337) and MEDI4736 in Subjects With Recurrent, Platinum-Resistant Ovarian Cancer for Whom Pegylated Liposomal Doxorubicin (PLD) is Indicated," ClinicalTrials.gov: NCT02431559, First Posted: May 1, 2015, Last Update: Aug. 7, 2018, https://clinicaltrials.gov/ct2/show/study/NCT02431559. Date Accessed, Mar. 25, 2019 (9 pages).
Ludwig Institute for Cancer Research, "A Phase 1/2 Study to Investigate the Safety, Biologic and Anti-tumor Activity of ONCOS-102 in Combination With Durvalumab in Subjects With Advanced Peritoneal Malignancies," ClinicalTrials.gov: NCT02963831, First Posted: Nov. 15, 2016, Last Update: Mar. 18, 2019, https://clinicaltrials.gov/ct2/show/study/NCT02963831. Date Accessed, Mar. 25, 2019 (8 pages).
Lukacs et al., "AMD3100, a CxCR4 Antagonist, Attenuates Allergic Lung Inflammation and Airway Hyperreactivity," American Journal of Pathology, vol. 16, No. 4, 2002 (pp. 1353-1360).
Lycera Corp., "Study of LYC-55716 in Adult Subjects With Locally Advanced or Metastatic Cancer," ClinicalTrials.gov: NCT02929862, First Posted: Oct. 11, 2016, Last Update: May 7, 2018, https://clinicaltrials.gov/ct2/show/study/NCT02929862. Date Accessed, Mar. 25, 2019 (6 pages).
M.D. Anderson Cancer Center, "Lirilumab and Azacitidine in Treating Patients With Refractory or Relapsed Acute Myeloid Leukemia," ClinicalTrials.gov: NCT02399917, First Posted: Mar. 26, 2015, Last Update: Nov. 30, 2018, https://clinicaltrials.gov/ct2/show/study/NCT02399917. Date Accessed, Mar. 18, 2019 (8 pages).
M.D. Anderson Cancer Center, "Lirilumab and Nivolumab With 5-Azacitidine in Patients With Myelodysplastic Syndromes (MDS)," ClinicalTrials.gov: NCT02599649, First Posted: Nov. 6, 2015, Last Update: Feb. 1, 2019, https://clinicaltrials.gov/ct2/show/study/NCT02599649. Date Accessed, Mar. 18, 2019 (8 pages).
M.D. Anderson Cancer Center, "Lirilumab With Rituximab for Relapsed, Refractory or High-risk Untreated Chronic Lymphocytic

(56) References Cited

OTHER PUBLICATIONS

Leukemia (CLL) Patients," ClinicalTrials.gov: NCT02481297, First Posted: Jun. 25, 2015, Last Update: Jul. 3, 2018, https://clinicaltrials.gov/ct2/show/study/NCT02481297. Date Accessed, Mar. 18, 2019 (7 pages).

M.D. Anderson Cancer Center, "Nivolumab and HPV-16 Vaccination in Patients With HPV-16 Positive Incurable Solid Tumors," ClinicalTrials.gov: NCT02426892, First Posted: Apr. 27, 2015, Last Update: Aug. 6, 2018, https://clinicaltrials.gov/ct2/show/NCT02426892. Date Accessed Nov. 29, 2018 (8 pages).

Ma et al., "The chemokine receptor CXCR4 is required for retention of B lineage and granulocytic precursors in the bone marrow microenvironment," Immunity, vol. 10, Apr. 1999 (pp. 463-471).

Maciejweski-Duval et al., "Altered chemotactic response to CXCL12 in patients carrying GATA2 mutations," Journal of Leukocyte Biology, vol. 99, No. 6. Epub Dec. 28, 2015 (pp. 1065-1076).

Maekawa et al., "Chemokine/Receptor Dynamics in the Regulation of Hematopoiesis," Internal Medicine, vol. 39, No. 2., 2000 (pp. 90-100).

Matthys et al.," AMD3100, a potent and specific antagonist of the stromal cell-derived factor-1 chemokine receptor CXCR4, inhibits autoimmune joint inflammation in IFN-gamma receptor-deficient mice," Journal of Immunology, vol. 167, No. 8, 2001 (p. 4686-4692).

Maximilian Diehn, "SABR-ATAC: A Trial of TGF-beta Inhibition and Stereotactic Ablative Radiotherapy for Early Stage Non-small Cell Lung Cancer," ClinicalTrials.gov: NCT02581787, First Posted: Oct. 21, 2015, Last Update: Feb. 5, 2019, https://clinicaltrials.gov/ct2/show/study/NCT02581787. Date Accessed, Mar. 25, 2019 (7 pages).

McCormick et al., "Impaired recruitment of Grk6 and beta-Arrestin 2 causes delayed internalization and desensitization of a WHIM syndrome-associated CXCR4 mutant receptor," PLoS One, vol. 4, 2009, (e8102).

McDermott et al., "A phase 1 clinical trial of long-term, low-dose treatment of WHIM syndrome with the CXCR4 antagonist plerixafor," Blood, vol. 123, No. 15, Apr. 10, 2014 (pp. 2308-2316).

McDermott et al., "The CXCR4 antagonist plerixafor corrects panleukopenia in patients with WHIM syndrome," Blood, vol. 118, No. 18, Sep. 2, 2011 (pp. 4957-4962).

McDermott et al.,"Severe congenital neutropenia resulting from G6PC3 deficiency with increased neutrophil CXCR4 expression and myelokathexis," Blood Journal, vol. 116, 2010 (pp. 2793-2802).

McDermott, D. "Whim Syndrome," National Organization for Rare Disorders, 2013, 2016, https://rarediseases.org/rare-diseases/whim-syndrome. Date Accessed Sep. 27, 2018 (10 pages).

MedImmune LLC, "A Phase 1 Study of MEDI0562 in Adult Subjects With Selected Advanced Solid Tumors," ClinicalTrials.gov: NCT02318394, First Posted: Dec. 17, 2014, Last Update: Jan. 29, 2018, https://clinicaltrials.gov/ct2/show/study/NCT02318394. Date Accessed, Mar. 18, 2019 (7 pages).

MedImmune LLC, "A Study in Adult Subjects With Select Advanced Solid Tumors," ClinicalTrials.gov: NCT02583165, First Posted: Oct. 22, 2015, Last Update: Jan. 8, 2019, https://clinicaltrials.gov/ct2/show/study/NCT02583165. Date Accessed, Mar. 18, 2019 (7 pages).

MedImmune LLC, "A Study to Evaluate MEDI0562 in Combination With Immune Therapeutic Agents in Adult Subjects With Advanced Solid Tumors," ClinicalTrials.gov: NCT02705482, First Posted: Mar. 10, 2016, Last Update: Feb. 19, 2019, https://clinicaltrials.gov/ct2/show/study/NCT02705482. Date Accessed, Mar. 18, 2019 (10 pages).

MedImmune LLC, "MEDI9447 Alone and in Combination With MED14736 in Adult Subjects With Select Advanced Solid Tumors," ClinicalTrials.gov: NCT02503774, First Posted: Jul. 21, 2015, Last Update: Mar. 11, 2019, https://clinicaltrials.gov/ct2/show/study/NCT02503774. Date Accessed, Mar. 18, 2019 (8 pages).

Merck KGaA, Darmstadt, Germany, "MSB0011359C (M7824) in Subjects With Metastatic or Locally Advanced Solid Tumors," ClinicalTrials.gov: NCT02699515, First Posted: Mar. 4, 2016, Last Update: Sep. 12, 2018, https://clinicaltrials.gov/ct2/show/study/NCT02699515. Date Accessed, Mar. 25, 2019 (8 pages).

Merck Sharp & Dohme Corp., "Study of MK-1454 Alone or in Combination With Pembrolizumab in Participants With Advanced/Metastatic Solid Tumors or Lymphomas (MK-1454-001)," ClinicalTrials.gov: NCT03010176, First Posted: Jan. 4, 2017, Last Update: Mar. 15, 2019, https://clinicaltrials.gov/ct2/show/study/NCT03010176. Date Accessed, Mar. 18, 2019 (11 pages).

Merck Sharp & Dohme Corp., "Study of MK-4166 and MK-4166 in Combination With Pembrolizumab (MK-3475) in Participants With Advanced Solid Tumors (MK-4166-001)," ClinicalTrials.gov: NCT02132754, First Posted: May 7, 2014, Last Update: Sep. 24, 2018, https://clinicaltrials.gov/ct2/show/study/NCT02132754. Date Accessed, Mar. 18, 2019 (6 pages).

Michael et al., "Exclusive and Persistent Use of the Entry Coreceptor CXCR4 by Human Immunodeficiency Virus Type 1 from a Subject Homozygous for CCR5 Δ32," Journal of Virology, vol. 72, No. 7, Jul. 1998 (pp. 6040-6047).

Miller, J. et al, "Novel N-substituted benzimidazole CXCR4 antagonists as potential anti-HIV agents," Bioorganic & Medicinal Chemistry Letters, vol. 20, 2010 (pp. 2125-2128).

Miller, J. et al, "Synthesis and SAR of novel isoquinoline CXCR4 antagonists with potent anti-HIV activity," vol. 20, 2010 (pp. 3026-3030).

Montane et al., "Prevention of murine autoimmune diabetes by CCL22-mediated Treg recruitment to pancreatic islets," Journal of Clinical Investigation, vol. 121, No. 8, Aug. 2011 (pp. 3024-3028).

Mosi R. M. et al., "The molecular pharmacology of AMD11070: An orally bioavailable CXCR4 HIV entry inhibitor," Biochemical Pharmacology, vol. 83, 2012 (pp. 472-479).

Moskovits N. et al., "p53 attenuates cancer cell migration and invasion through repression of SDF-1/CXCL12 expression in stromal fibroblasts," Cancer Research, vol. 66, No. 22, Nov. 15, 2006 (pp. 10671-10676).

Motzer et al., "Nivolumab for Metastatic Renal Cell Carcinoma: Results of a Randomized Phase II Trial," Journal of Clinical Oncology, vol. 33, No. 13, 2015 (pp. 1430-1437).

Motzer et al., "Nivolumab versus Everolimus in Advanced Renal-Cell Carcinoma," New England Journal of Medicine, vol. 373, No. 19, 2015 (pp. 1803-1813).

Moyle, et al., "Proof of Activity with AMD11070, an Orally Bioavailable Inhibitor of CXCR4-Tropic HIV Type 1," Clinical Infectious Diseases, vol. 48, 2009 (pp. 798-805).

Murdoch et al., "Chemokine receptors and their role in inflammation and infectious diseases," Blood, vol. 95, 2000 (pp. 3032-3043).

Nagaraj S. et al., "Altered recognition of antigen is a mechanism of CD8+ T cell tolerance in cancer," Natural Medicine, vol. 13, No. 7, Jul. 2007 (pp. 828-835).

Nagase et al., "Expression of CXCR4 in Eosinophils: Functional Analyses and Cytokine-Mediated Regulation," The Journal of Immunology, vol. 164, No. 11, 2000 (pp. 5935-5943).

Nanki et al., "Cutting Edge: Stromal Cell-Derived Factor-1 Is a Costimulator for CD4+ T Cell Activation," The Journal of Immunology, vol. 164, No. 10, 2000 (pp. 5010-5014).

Nash et al., "Allogeneic HSCT for autoimmune diseases: conventional conditioning regimens," Bone Marrow Transplantation, vol. 32, 2003 (pp. S77-S80).

National Cancer Institute (NCI), "A Phase I Study of Intravenous Recombinant Human IL-15 in Adults With Refractory Metastatic Malignant Melanoma and Metastatic Renal Cell Cancer," ClinicalTrials.gov: NCT01021059, First Posted: Nov. 26, 2009, Last Update: Feb. 26, 2019, https://clinicaltrials.gov/ct2/show/study/NCT01021059. Date Accessed, Mar. 20, 2019 (9 pages).

National Cancer Institute (NCI), "Anti-ICOS Monoclonal Antibody MEDI-570 in Treating Patients With Relapsed or Refractory Peripheral T-cell Lymphoma Follicular Variant or Angioimmunoblastic T-cell Lymphoma," ClinicalTrials.gov: NCT02520791, First Posted: Aug. 13, 2015, Last Update: Feb. 6, 2019, https://clinicaltrials.gov/ct2/show/study/NCT02520791. Date Accessed, Mar. 18, 2019 (13 pages).

National Cancer Institute (NCI), "Part 2 of Phase 1 Study of GC1008 to Treat Advanced Melanoma (Part 2 Will Only Accept and Treat Patients With Advanced Malignant Melanoma)," ClinicalTrials.

(56) References Cited

OTHER PUBLICATIONS gov: NCT00923169, First Posted: Jun. 18, 2009, Last Update: Mar. 12, 2019, https://clinicaltrials.gov/ct2/show/study/NCT00923169. Date Accessed, Mar. 25, 2019 (8 pages).
National Cancer Institute (NCI), "Subcutaneous Recombinant Human IL-15 (s.c. rhIL-15) and Alemtuzumab for People With Refractory or Relapsed Chronic and Acute Adult T-cell Leukemia (ATL)," ClinicalTrials.gov: NCT02689453, First Posted: Feb. 24, 2016, Last Update: Mar. 20, 2019, https://clinicaltrials.gov/ct2/show/study/NCT02689453. Date Accessed, Mar. 20, 2019 (9 pages).
National Cancer Institute (NCI), "Trametinib and Navitoclax in Treating Patients With Advanced or Metastatic Solid Tumors," ClinicalTrials.gov: NCT02079740, First Posted: Mar. 6, 2014, Last Update: Feb. 6, 2019, https://clinicaltrials.gov/ct2/show/study/NCT02079740. Date Accessed, Mar. 25, 2019 (12 pages).
National Cancer Institute (NCI), "Use of IL-15 After Chemotherapy and Lymphocyte Transfer in Metastatic Melanoma," ClinicalTrials.gov: NCT01369888, First Posted: Jun. 9, 2011, Last Update: Jan. 27, 2015, https://clinicaltrials.gov/ct2/show/study/NCT01369888. Date Accessed, Mar. 20, 2019 (9 pages).
National Cancer Institute, "Nivolumab and Ipilimumab in Treating Patients With HIV Associated Relapsed or Refractory Classical Hodgkin Lymphoma or Solid Tumors That Are Metastatic or Cannot Be Removed by Surgery," ClinicalTrials.gov: NCT02408861, First Posted: Apr. 6, 2016, Last Update: Jun. 12, 2018, https://clinicaltrials.gov/ct2/show/study/NCT02408861. Date Accessed, Nov. 29, 2018 (13 pages).
National Cancer Institute, "Nivolumab in Treating Patients With HTLV-Associated T-Cell Leukemia/Lymphoma," ClinicalTrials.gov: NCT02631746, First Posted: Dec. 16, 2015, Last Update: Aug. 28, 2018, https://clinicaltrials.gov/ct2/show/study/NCT02631746. Date Accessed, Nov. 29, 2018 (9 pages).
Neumedicines Inc., "NM-IL-12 (rHuIL-12) In Relapsed/Refractory Diffuse Large B-Cell Lymphoma (DLBCL) Undergoing Salvage Chemotherapy," ClinicalTrials.gov: NCT02544724, First Posted: Sep. 9, 2015, Last Update: Aug. 3, 2016, https://clinicaltrials.gov/ct2/show/study/NCT02544724. Date Accessed, Mar. 20, 2019 (8 pages).
Neumedicines Inc., "NM-IL-12 in Cutaneous T-Cell Lymphoma (CTCL) Undergoing Total Skin Electron Beam Therapy (TSEBT)," ClinicalTrials.gov: NCT02542124, First Posted: Sep. 4, 2015, Last Update: Nov. 16, 2018, https://clinicaltrials.gov/ct2/show/study/NCT02542124. Date Accessed, Mar. 20, 2019 (8 pages).
Neves, M. et al., Ligand-guided optimization of CXCR4 homology models for virtual screening using a multiple chemotype approach, Journal of Computer-Aided Molecular Design, vol. 24, No. 12, Oct. 20, 2010 (pp. 1023-1033).
Nicholas Butowski, "A Study of Varlilumab and IMA950 Vaccine Plus Poly-ICLC in Patients With WHO Grade II Low-Grade Glioma (LGG)," ClinicalTrials.gov: NCT02924038, First Posted: Oct. 5, 2016, Last Update: Mar. 6, 2019, https://clinicaltrials.gov/ct2/show/study/NCT02924038. Date Accessed, Mar. 18, 2019 (9 pages).
No author listed, SciFinder Search Results, No month listed, 2015 (39 pages).
No author listed, SciFinder Search Results, No month listed, 2015 (9 pages).
Novartis Pharmaceuticals, "A Phase I/Ib Study of NIZ985 in Combination With PDR001 in Adults With Metastatic Cancers," ClinicalTrials.gov: NCT02452268, First Posted: May 22, 2015, Last Update: Oct. 2, 2018, https://clinicaltrials.gov/ct2/show/study/NCT02452268. Date Accessed, Mar. 20, 2019 (7 pages).
Novartis Pharmaceuticals, "Phase I/Ib Study of GWN323 Alone and in Combination With PDR001 in Patients With Advanced Malignancies and Lymphomas," ClinicalTrials.gov: NCT02740270, First Posted: Apr. 15, 2016, Last Update: Feb. 18, 2019, https://clinicaltrials.gov/ct2/show/study/NCT02740270. Date Accessed, Mar. 28, 2019 (6 pages).
Novartis Pharmaceuticals, "Phase I/Ib Study of NIS793 in Combination With PDR001 in Patients With Advanced Malignancies.," ClinicalTrials.gov: NCT02947165, First Posted: Oct. 27, 2016, Last Update: Nov. 6, 2018, https://clinicaltrials.gov/ct2/show/study/NCT02947165. Date Accessed, Mar. 25, 2019 (9 pages).
Novartis Pharmaceuticals, "Phase I/II Study of BLZ945 Single Agent or BLZ945 in Combination With PDR001 in Advanced Solid Tumors," ClinicalTrials.gov: NCT02829723, First Posted: Jul. 12, 2016, Last Update: Jul. 12, 2018, https://clinicaltrials.gov/ct2/show/study/NCT02829723. Date Accessed, Mar. 18, 2019 (7 pages).
Novartis Pharmaceuticals, "Safety and Efficacy of MBG453 as Single Agent and in Combination With PDR001 in Patients With Advanced Malignancies," ClinicalTrials.gov: NCT02608268, First Posted: Nov. 18, 2015, Last Update: Oct. 2, 2018, https://clinicaltrials.gov/ct2/show/study/NCT02608268. Date Accessed, Mar. 25, 2019 (10 pages).
Novartis Pharmaceuticals, "Study of the Safety and Efficacy of MIW815 With PDR001 to Patients With Advanced/Metastatic Solid Tumors or Lymphomas," ClinicalTrials.gov: NCT03172936, First Posted: Jun. 1, 2017, Last Update: Feb. 18, 2019, https://clinicaltrials.gov/ct2/show/study/NCT03172936. Date Accessed, Mar. 18, 2019 (9 pages).
Nyunt, et al., "Pharmacokinetic Effect of AMD070, an Oral CXCR4 Antagonist, on CYP3A4 and CYP2D6 Substrates Midazolam and Dextromethorphan in Healthy Volunteers," Journal of Acquired Immune Deficiency Syndrome, vol. 47, 2008 (pp. 559-565).
O'Boyle et al., "Inhibition of CXCR4-CXCL12 chemotaxis in melanoma by AMD11070," British Journal of Cancer, vol. 108, No. 8, Apr. 2013 (pp. 1634-1640).
O'Hagen et al., "Apoptosis Induced by Infection of Primary Brian Cultures with Diverse Human Immunodeficiency Virus Type 1 Isolates: Evidence for a Role of the Envelope," Journal of Virology, vol. 73, No. 2, Feb. 1999 (pp. 897-906).
Okazaki, T. et al., "A rheostat for immune responses: the unique properties of PD1 and their advantages for clinical application," Nature Immunology, vol. 14, No. 12, Dec. 2013 (pp. 1212-1218).
Oncolytics Biotech, "A Study of REOLYSIN® in Combination With Gemcitabine in Patients With Advanced Pancreatic Adenocarcinoma," ClinicalTrials.gov: NCT00998322, First Posted: Oct. 20, 2009, Last Update: Apr. 10, 2015, https://clinicaltrials.gov/ct2/show/study/NCT00998322. Date Accessed, Mar. 25, 2019 (6 pages).
Oncolytics Biotech, "Efficacy Study of REOLYSIN® in Combination With Paclitaxel and Carboplatin in Platinum-Refractory Head and Neck Cancers," ClinicalTrials.gov: NCT01166542, First Posted: Jul. 21, 2010, Last Update: Nov. 5, 2014, https://clinicaltrials.gov/ct2/show/study/NCT01166542. Date Accessed, Mar. 25, 2019 (7 pages).
Oncolytics Biotech, "Phase 2 Study of REOLYSIN® in Combination With Paclitaxel and Carboplatin for Non-Small Cell Lung Cancer With KRAS or EGFR Activation," ClinicalTrials.gov: NCT00861627, First Posted: Mar. 13, 2009, Last Update: Dec. 2, 2015, https://clinicaltrials.gov/ct2/show/study/NCT00861627. Date Accessed, Mar. 25, 2019 (7 pages).
OncoMed Pharmaceuticals, Inc., "A Study of OMP-313M32 in Subjects With Locally Advanced or Metastatic Solid Tumors," ClinicalTrials.gov: NCT03119428, First Posted: Apr. 18, 2017, Last Update: Dec. 7, 2018, https://clinicaltrials.gov/ct2/show/study/NCT03119428. Date Accessed, Mar. 25, 2019 (7 pages).
Panka, DJ. et al., "HDM2 antagonism delays the development of sunitinib resistance in RCC xenografts: Effects of MI-319 on sunitinib-induced p53 activation, SDF-1 induction, and tumor infiltration by CDllb+/Gr-l+ myeloid suppressor cells," Molecular Cancer, vol. 12, No. 17, 2013 (pp. 1-12).
Parameswaran et al., "Combination of drug therapy in acute lymphblastic leukemia with CXCR4 antagonist," Leukemia, vol. 25, No. 8, Aug. 1, 2011 (pp. 1314-1323).
Peled et al., "The chemokine SDF-1 activates the integrins LFA-1, VLA-4, and VLA-5 on immature human CD34(+) cells: role in transendothelial/stromal migration and engraftment of NOD/SCID mice," Blood, vol. 95, No. 11, 2000 (pp. 3289-3296).
Pfizer, "A Study Of Avelumab In Combination With Other Cancer Immunotherapies In Advanced Malignancies (Javelin Medley)," ClinicalTrials.gov: NCT02554812, First Posted: Sep. 18, 2015, Last Update: Mar. 13, 2019, https://clinicaltrials.gov/ct2/show/study/NCT02554812. Date Accessed, Mar. 18, 2019 (13 pages).

(56) References Cited

OTHER PUBLICATIONS

Pfizer, "Avelumab In Combination Regimens That Include An Immune Agonist, Epigenetic Modulator, CD20 Antagonist and/or Conventional Chemotherapy in Patients With Relapsed or Refractory Diffuse Large B-cell Lymphoma (R/R DLBCL) (Javelin DLBCL)," ClinicalTrials.gov: NCT02951156, First Posted: Nov. 1, 2016, Last Update: Jan. 29, 2019, https://clinicaltrials.gov/ct2/show/study/NCT02951156. Date Accessed, Mar. 18, 2019 (11 pages).

Pike et al., "Nutrition: An Integrated Approach," Third Edition, John Wiley & Sons, 1984 (pp. 538-539).

Plexxikon, "A Combination Clinical Study of PLX3397 and Pembrolizumab To Treat Advanced Melanoma and Other Solid Tumors," ClinicalTrials.gov: NCT02452424, First Posted: May 22, 2015, Last Update: Nov. 15, 2018, https://clinicaltrials.gov/ct2/show/study/NCT02452424. Date Accessed, Mar. 18, 2019 (9 pages).

Ponath et al., "Chemokine receptor antagonists: novel therapeutics for inflammation and AIDS," Expert Opinion on Investigational Drugs, vol. 7, No. 1, 1998 (pp. 1-18).

Providence Health & Services, "Anti-OX40 Antibody (MEDI6469) in Patients With Metastatic Colorectal Cancer," ClinicalTrials.gov: NCT02559024, First Posted: Sep. 24, 2015, Last Update: Oct. 10, 2018, https://clinicaltrials.gov/ct2/show/study/NCT02559024. Date Accessed, Mar. 18, 2019 (6 pages).

Providence Health & Services, "Anti-OX40 Antibody in Head and Neck Cancer Patients," ClinicalTrials.gov: NCT02274155, First Posted: Oct. 24, 2014, Last Update: Nov. 26, 2018, https://clinicaltrials.gov/ct2/show/study/NCT02274155. Date Accessed, Mar. 18, 2019 (6 pages).

Providence Health & Services, "Anti-OX40, Cyclophosphamide (CTX) and Radiation in Patients With Progressive Metastatic Prostate Cancer," ClinicalTrials.gov: NCT01303705, First Posted: Feb. 25, 2011, Last Update: Aug. 29, 2018, https://clinicaltrials.gov/ct2/show/study/NCT01303705. Date Accessed, Mar. 18, 2019 (10 pages).

Providence Health & Services, "Stereotactic Body Radiation and Monoclonal Antibody to OX40 (MEDI6469) in Breast Cancer Patients With Metastatic Lesions (OX40 Breast)," ClinicalTrials.gov: NCT01862900, First Posted: May 27, 2013, Last Update: Mar. 6, 2019, https://clinicaltrials.gov/ct2/show/study/NCT01862900. Date Accessed, Mar. 18, 2019 (7 pages).

PsiOxus Therapeutics Ltd, "Phase I / Dose Expansion Study of Enadenotucirev in Ovarian Cancer Patients (OCTAVE)," ClinicalTrials.gov: NCT02028117, First Posted: Jan. 6, 2014, Last Update: Feb. 26, 2019, https://clinicaltrials.gov/ct2/show/study/NCT02028117. Date Accessed, Mar. 25, 2019 (8 pages).

PsiOxus Therapeutics Ltd, "Phase I Study of Enadenotucirev and PD-1 Inhibitor in Subjects With Metastatic or Advanced Epithelial Tumors (SPICE)," ClinicalTrials.gov: PsiOxus Therapeutics Ltd, First Posted: Dec. 21, 2015, Last Update: Mar. 4, 2019, https://clinicaltrials.gov/ct2/show/study/NCT02636036. Date Accessed, Mar. 25, 2019 (9 pages).

PubChem Open Chemistry Database, Compound Summary for CID 10890081, created Oct. 25, 2006 (14 pages).

PubChem Open Chemistry Database, Compound Summary for CID 12087079, created Feb. 7, 2007 (14 pages).

PubChem Open Chemistry Database, Compound Summary for CID 19046926, created Dec. 4, 2017 (11 pages).

PubChem Open Chemistry Database, Compound Summary for SID 219642471, created Oct. 21, 2014 (12 pages).

PubChem Open Chemistry Database, Compound Summary for CID 70962830, created Mar. 21, 2013 (12 pages).

Raman et al., "Immunotherapy in Metastatic Renal Cell Carcinoma: A Comprehensive Review," Biomed Research International, vol. 2015, 2015 (pp. 1-9).

Rana et al., "Role of CCR5 in infection of primary macrophages and lymphocytes by macrophage-tropic strains of human immunodeficiency virus: resistance to patient-derived and prototype isolates resulting from the delta ccr5 mutation," Journal of Virology, vol. 71, No. 4, 1997 (pp. 3219-3227).

Ratajczak, et al., "The pleotropic effects of the SDF-1—CXCR4 axis in organogenesis, regeneration, and tumorigenesis," Leukemia, vol. 20, 2006 (pp. 1915-1924).

Reagen-Shaw et al., "Dose translation from animal to human studies revisited," The FASEB Journal, vol. 22, Mar. 2007 (pp. 659-661).

Reetz et al., "Highly Efficient Lipase-Catalyzed Kinetic Resolution of Chiral Amines" Chimia International Journal for Chemistry, vol. 48, No. 12, 1994 (p. 570).

Regeneron Pharmaceuticals, "An Exploratory Tumor Biopsy-driven Study to Understand the Relationship Between Biomarkers and Clinical Response in Melanoma Patients Receiving REGN2810 (Anti-PD-1)," ClinicalTrials.gov: NCT03002376, First Posted: Dec. 23, 2016, Last Update: Jan. 11, 2019, https://clinicaltrials.gov/ct2/show/study/NCT03002376. Date Accessed, Mar. 25, 2019 (6 pages).

Regeneron Pharmaceuticals, "PD-1 in Patients With Advanced Basal Cell Carcinoma Who Experienced Progression of Disease on Hedgehog Pathway Inhibitor Therapy, or Were Intolerant of Prior Hedgehog Pathway Inhibitor Therapy," ClinicalTrials.gov: NCT03132636, First Posted: Apr. 28, 2017, Last Update: Oct. 2, 2018, https://clinicaltrials.gov/ct2/show/study/NCT03132636. Date Accessed, Mar. 25, 2019 (6 pages).

Regeneron Pharmaceuticals, "Study of REGN 2810 Compared to Platinum-Based Chemotherapies in Participants With Metastatic Non-Small Cell Lung Cancer (NSCLC)," ClinicalTrials.gov: NCT03088540, First Posted: Mar. 23, 2017, Last Update: Nov. 5, 2018, https://clinicaltrials.gov/ct2/show/study/NCT03088540. Date Accessed, Mar. 25, 2019 (9 pages).

Regeneron Pharmaceuticals, "Study of REGN2810 and REGN1979 in Patients With Lymphoma," ClinicalTrials.gov: NCT02651662, First Posted: Jan. 11, 2016, Last Update: Sep. 11, 2018, https://clinicaltrials.gov/ct2/show/study/NCT02651662. Date Accessed, Mar. 25, 2019 (7 pages).

Regeneron Pharmaceuticals, "Study of REGN2810 in Patients With Advanced Cutaneous Squamous Cell Carcinoma," ClinicalTrials.gov: NCT02760498, First Posted: May 3, 2016, Last Update: Jan. 14, 2019, https://clinicaltrials.gov/ct2/show/study/NCT02760498. Date Accessed, Mar. 25, 2019 (6 pages).

Regeneron Pharmaceuticals, "Study of REGN3767 (Anti-LAG-3) With or Without REGN2810 (Anti-PD1) in Advanced Cancers," ClinicalTrials.gov: NCT03005782, First Posted: Dec. 29, 2016, Last Update: Jun. 18, 2018, https://clinicaltrials.gov/ct2/show/study/NCT03005782. Date Accessed, Mar. 25, 2019 (7 pages).

Righi E. et al., "CXCL12/CXCR4 Blockade Induces Multimodal Antitumor Effects That Prolong Survival in an Immunocompetent Mouse Model of Ovarian Cancer," Cancer Research, vol. 71, No. 16, Aug. 15, 2011 (pp. 5522-5534).

Rini et al., "Comparative effectiveness of axitinib versus soragenib in advanced renal cell carcinoma (AXIS): a randomised phase 3 trial," Lancet, vol. 378, 2011 (pp. 1931-1939).

Robert Lowsky, "A Phase I/II Study of Intratumoral Injection of SD-101," ClinicalTrials.gov: NCT02254772, First Posted: Oct. 2, 2014, Last Update: Sep. 29, 2017, https://clinicaltrials.gov/ct2/show/study/NCT02254772. Date Accessed, Mar. 25, 2019 (9 pages).

Robert, et al., "Pembrolizumab versus Ipilimumab in Advanced Melanoma," New England Journal of Medicine, vol. 372, 2015 (pp. 2521-2532).

Salcedo et al., "Vascular endothelial growth factor and basic fibroblast growth factor induce expression of CXCR4 on human endothelial cells: In vivo neovascularization induced by stromal-derived factor-1alpha.Am," The American Journal of Pathology, vol. 154, No. 4, 1999 (pp. 1125-1135).

Saxena et al., "Efficacy and Mechanism of Action of CXCR4 Inhibition in B16 OVA Melanoma Model," The Society for Immunotherapy of Cancer Annual Meeting, National Harbor, Maryland, Nov. 8-12, 2017 (1 page).

Saxena et al., "Efficacy and Mechanism of Action of CXCR4 Inhibition in B16-OVA Melanoma Model," Journal for ImmunoTherapy of Cancer, Abstract, vol. 5, Suppl. 2, 2017 (p. 356).

Scala, et al., "Expression of CXCR4 predicts poor prognosis in patients with malignant melanoma," Clinical Cancer Research, vol. 11, Mar. 1, 2005 (pp. 1835-1841).

(56) References Cited

OTHER PUBLICATIONS

Scala et al., "Molecular Pathways: Targeting the CXCR4-CXCL12 Axis—Untapped Potential in the Tumor Microenvironment," Clinical Cancer Research, vol. 21, No. 19, Jul. 21, 2015 (pp. 4278-4285).
Schlabach et al., "Cancer proliferation gene discovery through functional genomics," Science, vol. 319, No. 5863, Feb. 1, 2008 (pp. 620-624).
Schols et al., "Bicyclams, a class of potent anti-HIV agents, are targeted at the HIV coreceptor for Fusin/CXCR-4," Antiviral Research, vol. 35, 1997 (pp. 147-156).
Schols et al., "Inhibition of T-tropic HIV Strains by Selective Antagonization of the Chemokine Receptor CXCR4J," Journal of Experimental Medicine, vol. 186, No. 8, 1997 (pp. 1383-1388).
Schramm et al., "Cytopathicity of Human Immunodeficiency Virus Type 2 (HIV-2) in Human Lymphoid Tissue Is Coreceptor Dependent and Comparable to That of HIV-1," Journal of Virology, vol. 74., No. 20, 2000 (pp. 184-192).
Schuitemaker et al., "Biological phenotype of human immunodeficiency virus type 1 clones at different stages of infection: progression of disease is associated with a shift from monocytotropic to T-cell-tropic virus population," Journal of Virology, vol. 66, No. 3, 1992 (pp. 1354-1360).
Sharma, P. et al., "Primary, Adaptive, and Acquired Resistance to Cancer Immunotherapy," Cell, vol. 168, No. 4, Feb. 9, 2017 (pp. 707-723).
Shen et al., "CXCR4-mediated STAT3 activation is essential for CXCL12-induced invasion in bladder cancer," Tumour Biology, vol. 34, 2013 (pp. 1839-1845).
Shojaei F. et al., "Tumor refractoriness to anti-VEGF treatment is mediated by CD11b+Grl+ myeloid cells," Nature Biotechnology, vol. 25, No. 8, Aug. 2007 (pp. 911-920).
Sidney Kimmel Comprehensive Cancer Center at Johns Hopkins, "Anti-LAG-3 Alone & in Combination w/ Nivolumab Treating Patients w/ Recurrent GBM (Anti-CD137 Arm Closed Oct. 16, 2018)," ClinicalTrials.gov: NCT02658981, First Posted: Jan. 20, 2016, Last Update: Feb. 11, 2019, https://clinicaltrials.gov/ct2/show/study/NCT02658981. Date Accessed, Mar. 18, 2019 (13 pages).
Sidney Kimmel Comprehensive Cancer Center at Johns Hopkins, "Pilot Study With CY, Pembrolizumab, GVAX, and IMC-CS4 (LY3022855) in Patients With Borderline Resectable Adenocarcinoma of the Pancreas," ClinicalTrials.gov: NCT03153410, First Posted: May 15, 2017, Last Update: Mar. 19, 2019, https://clinicaltrials.gov/ct2/show/study/NCT03153410. Date Accessed, Mar. 18, 2019 (8 pages).
SillaJen, Inc., "Hepatocellular Carcinoma Study Comparing Vaccinia Virus Based Immunotherapy Plus Sorafenib vs Sorafenib Alone (PHOCUS)," ClinicalTrials.gov: NCT02562755, First Posted: Sep. 29, 2015, Last Update: Feb. 6, 2019, https://clinicaltrials.gov/ct2/show/study/NCT02562755. Date Accessed, Mar. 25, 2019 (7 pages).
Silva et al., "Profiling essential genes in human mammary cells by multiplex RNA1 screening," Science, vol. 319, Feb. 1, 2008 (pp. 617-620).
Simmons et al., "CXCR4 as a Functional Coreceptor for Human Immunodeficiency Virus Type 1 Infection of Primary Macrophages," Journal of Virology, vol. 72, No. 10, 1998 (pp. 8453-8457).
Simmons et al., "Primary, syncytium-inducing human immunodeficiency virus type 1 isolates are dual-tropic and most can use either Lestr or CCR5 as coreceptors for virus entry," Journal of Virolology, vol. 70, No. 12, 1996 (pp. 8355-8360).
SK Chemicals Co., Ltd., "Study to Evaluate SID 530 Compared to Taxotere," ClinicalTrials.gov: NCT00931008, First Posted: Jul. 2, 2009, Last Update: Jan. 24, 2013, https://clinicaltrials.gov/ct2/show/study/NCT00931008. Date Accessed, Mar. 25, 2019 (6 pages).
Skerlj R. et al., "Discovery of Novel Small Molecule Orally Bioavailable C-X-C Chemokine Receptor 4 Antagonists That Are Potent Inhibitors of T-Tropic (X4) HIV-1 Replication," Journal of Medicinal Chemistry, vol. 53, No. 8, 2010 (pp. 3376-3388).
Stone, et al., "Multiple-Dose Escalation Study of the Safety, Pharmacokinetics, and Biologic Activity of Oral AMD070, a Selective CXCR4 Receptor Inhibitor, in Human Subjects.," Antimicrobial Agents and Chemotherapy, vol. 51, No. 7, Jul. 2007 (pp. 2351-2358).
Sullivan et al., "Pembrolizumab for Treatment of Patients with Advanced or Unresectable Melanoma," Clincal Cancer Research, vol. 12, No. 13, Apr. 30, 2015 (pp. 2892-2897).
Supplementary European Search Report issued by the European Patent Office for European Patent App. No. 02775823.4, dated Dec. 23, 2004 (3 pages).
Supplementary European Search Report issued by the European Patent Office for European Patent App. No. 02805977.2, dated Apr. 16, 2008 (3 pages).
Supplementary European Search Report issued by the European Patent Office for European Patent App. No. 04752905.2, dated Mar. 12, 2010 (6 pages).
Supplementary European Search Report issued by the European Patent Office for European Patent App. No. 04814091.7, dated Mar. 10, 2008 (4 pages).
Supplementary European Search Report issued by the European Patent Office for European Patent App. No.04760161.2, dated Jun. 10, 2008 (3 pages).
Syndax Pharmaceuticals, "A Phase 2 Multi-Center Study of Entinostat (SNDX-275) in Patient With Relapsed or Refractory Hodgkin's Lymphoma," ClinicalTrials.gov: NCT00866333, First Posted: Mar. 20, 2009, Last Update: Jul. 1, 2016, https://clinicaltrials.gov/ct2/show/study/NCT00866333. Date Accessed, Mar. 20, 2019 (6 pages).
Targovax Oy, "A Pilot Study of Sequential ONCOS-102, an Engineered Oncolytic Adenovirus Expressing GMCSF, and Pembrolizumab in Patients With Advanced or Unresectable Melanoma Progressing After Programmed Cell Death Protein 1 (PD1) Blockade," ClinicalTrials.gov: NCT03003676, First Posted: Dec. 28, 2016, Last Update: Oct. 25, 2018, https://clinicaltrials.gov/ct2/show/study/NCT03003676. Date Accessed, Mar. 25, 2019 (8 pages).
Tarhini, et al., "Immune Monitoring of the Circulation and the Tumor Microenvironment in Patients with Regionally Advanced Melanoma Receiving Neoadjuvant Ipilimumab," PLoS One, vol. 9, No. 2, Feb. 2014 (p. e87705).
Teasdale et al., "Risk Assessment of Genotoxic Impurities in New Chemical Entities: Strategies To Demonstrate Control," Organic Process Research and Development, vol. 17, 2013 (p. 221-230).
Tersmette et al., "Differential Syncytium-Inducing Capacity of Human Immunodeficiency Virus Isolates: Frequent Detection of Syncytium-Inducing Isolates in Patients with Aquired Immune Deficiency Syndrome (AIDS) and AIDS-Related Complex," Journal of Virology, vol. 62, No. 6. (pp. 2026-2032).
Tesaro, Inc., "A Phase 1 Study of TSR-022, an Anti-TIM-3 Monoclonal Antibody, in Patients With Advanced Solid Tumors (AMBER)," ClinicalTrials.gov: NCT02817633, First Posted: Jun. 29, 2016, Last Update: Mar. 19, 2019, https://clinicaltrials.gov/ct2/show/study/NCT02817633. Date Accessed, Mar. 25, 2019 (8 pages).
Therasse et al., "New Guidelines to Evaluate the Response to Treatment in Solid Tumors," Journal of the National Cancer Institute, vol. 92, No. 3, Feb. 2, 2000 (pp. 205-216).
Tortorici et al., "Influence of mild and moderate hepatic impairment on axitinib pharmacokinetics," Investigational New Drugs, vol. 29, 2011 (pp. 1370-1380).
Toyozawa, et al., "Chemokine receptor CXCR4 is a novel marker for the progression of cutaneous malignant melanoma," Japan Society of Histochemisty and Cytochemistry, vol. 45, No. 5, 2012 (pp. 293-299).
Trillium Therapeutics Inc., "A Trial of TTI-621 for Patients With Hematologic Malignancies and Selected Solid Tumors," ClinicalTrials.gov: NCT02663518, First Posted: Jan. 26, 2016, Last Update: Oct. 29, 2018, https://clinicaltrials.gov/ct2/show/study/NCT02663518. Date Accessed, Mar. 18, 2019 (9 pages).
Trillium Therapeutics Inc., "Trial of Intratumoral Injections of TTI-621 in Subjects With Relapsed and Refractory Solid Tumors and Mycosis Fungoides," ClinicalTrials.gov: NCT02890368, First Posted: Sep. 7, 2016, Last Update: Mar. 13, 2019, https://clinicaltrials.gov/ct2/show/study/NCT02890368. Date Accessed, Mar. 18, 2019 (9 pages).
Tu S.P. et al., "Curcumin induces the differentiation of myeloid-derived suppressor cells and inhibits their interaction with cancer

(56) References Cited

OTHER PUBLICATIONS cells and related tumor growth," Cancer Prevention Research, vol. 5, No. 2, Feb. 2012 (pp. 205-215).
Tumeh, et al., "PD-1 blockade induces responses by inhibiting adaptive immune resistance," Nature, vol. 515, No. 7528, Nov. 2014 (pp. 568-571).
U.S. Appl. No. 16/215,963, filed Dec. 11, 2018 (132 pages).
U.S. Appl. No. 16/311,020, filed Dec. 18, 2018 (237 pages).
U.S. Appl. No. 16/311,083, filed Dec. 18, 2018 (276 pages).
University of Southern California, "Axitinib With or Without Anti-OX40 Antibody PF-04518600 in Treating Patients With Metastatic Kidney Cancer," ClinicalTrials.gov: NCT03092856, First Posted: Mar. 28, 2017, Last Update: Aug. 13, 2018, https://clinicaltrials.gov/ct2/show/study/NCT03092856. Date Accessed, Mar. 18, 2019 (11 pages).
University of Texas Southwestern Medical Center, "Phase 2 Study of IDH305 in Low Grade Gliomas," ClinicalTrials.gov: NCT02987010, First Posted: Dec. 8, 2016, Last Update: Oct. 11, 2017, https://clinicaltrials.gov/ct2/show/study/NCT02987010. Date Accessed, Mar. 25, 2019 (7 pages).
Vanharanta et al., "Epigenetic expansion of VHL-HIF signal output drives multiorgan metastasis in renal cancer," Natural Medicine, vol. 19, No. 1., Jan. 2013 (pp. 50-56).
VentiRx Pharmaceuticals Inc., "A Phase Ib Study of Neoadjuvant of Cetuximab Plus Motolimod and Cetuximab Plus Motolimod Plus Nivolumab," ClinicalTrials.gov: NCT02124850, First Posted: Apr. 28, 2014, Last Update: Jul. 22, 2016, https://clinicaltrials.gov/ct2/show/study/NCT02124850. Date Accessed, Mar. 25, 2019 (6 pages).
Ward et al., "Genetic and molecular diagnosis of severe congenital neutropenia," Current Opinion in Hematology, vol. 16, No. 1, Jan. 2009 (pp. 9-13).
Wong, "Comparison of the potential multiple binding modes of bicyclam, monocyclam, and noncyclam small molecule CXC chemokine receptor 4 inhibitors," Molecular Pharmacology, vol. 74, No. 6, 2008 (pp. 1485-1495).
Zea A.H. et al. "Arginase-producing myeloid suppressor cells in renal cell carcinoma patients: a mechanism of tumor evasion," Cancer Research, vol. 65, No. 8, 2005 (pp. 3044-3048).
Zhang et al. "Preferential involvement of CXCR4 and CXCL12 in T cell migration toward melanoma cells," Cancer Biology & Therapy, vol. 5, No. 10, Oct. 2006 (pp. 1034-1312).
Zhang et al., "Chemokine Coreceptor Usage by Diverse Primary Isolates of Human Immunodeficiency Virus Type 1," Journal of Virology, vol. 72, No. 11, 1998 (pp. 9307-9312).
Zhang et al., "Will Multiple Coreceptors Need To Be Targeted by Inhibitors of Human Immunodeficiency Virus Type 1 Entry?," Journal of Virology, vol. 73, No. 4., 1999 (pp. 3443-3448).
Zhao et al., "TNF signaling drives myeloid-derived suppressor cell accumulation," Journal of Clinical Investigation, vol. 122, No. 11, Nov. 2012 (pp. 4094-4104).
Zlotnik et al., "Chemokines: a new classification system and their role in immunity," Immunity, vol. 12, Feb. 2000 (pp. 121-127).
Zou et al., "PD-L1 (B7-H1) and PD-1 Pathway Blockade for Cancer Therapy: Mechanisms, Response Biomarkers and Combinations," Science Translatonal Medicine, vol. 8., No. 328, Mar. 2016 (pp. 1-34).
Zuelzer, "'Myelokathexis'—A New Form of Chronic Granulocytopenia. Report of a case," New England Journal of Medicine, vol. 270, No. 14, 1964 (pp. 699-704).
Dudley et al., 2010, "CD8+ Enriched "Young" Tumor Infiltrating Lymphocytes Can Mediate Regression of Metastatic Melanoma," Clinical Cancer Research, 16(24):6122-6131.
Gao et al., 2007, "Intratumoral Balance of Regulatory and Cytotoxic T Cells Is Associated With Prognosis of Hepatocellular Carcinoma After Resection," Journal of Clinical Oncology 25(18):2586-2593.
Gassenmeier et al., 2013, "CXC Chemokine Receptor 4 is Essential for Maintenance of Renal cell Carcinoma-Initiating Cells and Predicts Metastasis," Stem Cells Journals 31(8):1467-1476.
PCT International Search Report and Written Opinion from PCT/US2017/026819 dated Jul. 21, 2017.
PCT International Search Report and Written Opinion from PCT/US2017/038590 dated Oct. 17, 2017.
PCT International Search Report and Written Opinion from PCT/US2017/038609 dated Oct. 31, 2017.
PCT International Search Report and Written Opinion from PCT/US2017/038613 dated Dec. 28, 2017.
PCT International Search Report and Written Opinion from PCT/US2018/038776 dated Nov. 20, 2018.
PCT International Search Report and Written Opinion from PCT/US2018/059482 dated Jan. 17, 2019.
PCT International Search Report and Written Opinion from PCT/US2019/027169 dated Jul. 3, 2019.
PCT International Search Report and Written Opinion from PCT/US2019/049065 dated Nov. 15, 2019.

Figure 1: X4P-001 Inhibition of SFD-1α Binding to CXCR4⁺CEM-CCRF Cells

Figure 2: X4P-001 Inhibition of SDF-1α Stimulated Eu-GTP Binding

Figure 3: X4P-001 Inhibition of SDF-1α Stimulated [$^{35}$S]-GTPγS Binding

Figure 4: X4P-001 Inhibition of SDF-1α-Induced Calcium Flux

Figure 5: X4P-001 Inhibition of SDF-1α Stimulated CCRF-CEM Chemotaxis

Figure 6: SDF-1α Stimulation of Calcium Flux in Wild Type and CXCR4 Variants

Figure 7: X4P-001 Inhibition of SDF-1α Stimulation in Wild Type and CXCR4 Variants Figure 8: WBC (A), Neutrophil (B), and Lymphocyte (C) Counts Following Oral Administration of X4P-001 to Male Beagle Dogs Figure 9
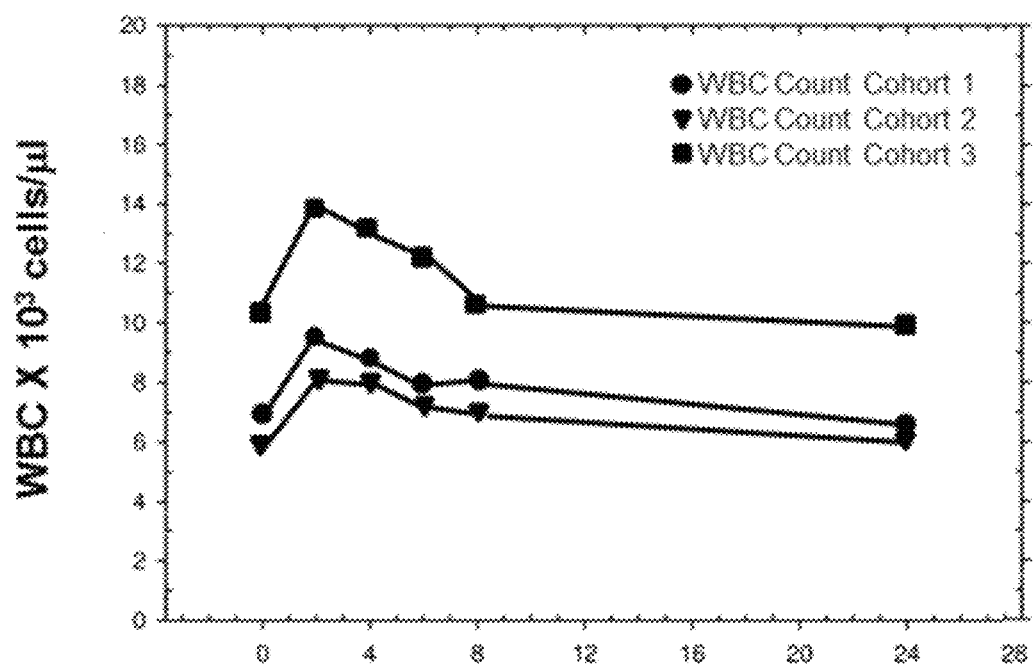
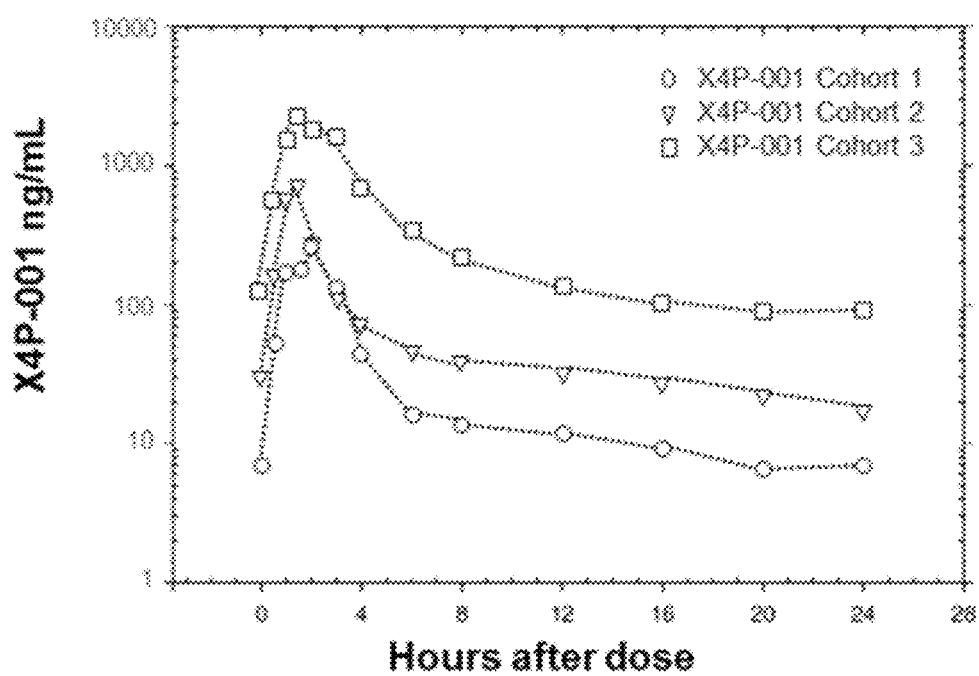

METHODS FOR TREATING IMMUNODEFICIENCY DISEASE

CROSS-REFERENCE TO RELATED APPLICATIONS

This application claims the benefit of priority to U.S. Provisional Patent Application serial numbers U.S. Ser. No. 62/271,087, filed Dec. 22, 2015, and U.S. Ser. No. 62/428,964, filed Dec. 1, 2016, the entirety of each of which is hereby incorporated by reference.

FIELD OF THE INVENTION

The present invention relates to methods for treating immunodeficiency disease, in particular, methods for treating warts, hypogammaglobulinemia, immunodeficiency, myelokathexis (WHIM) syndrome, or "WHIMS." WHIMS is a disease characterized by neutropenia and lymphopenia resulting in skin and genital warts and recurring infections.

BACKGROUND OF THE INVENTION

WHIM syndrome is a rare autosomal dominant immunodeficiency disorder which results in multiple mutations that remove 10-19 amino acids from the carboxy-terminus of CXCR4, a chemokine receptor expressed by both hematopoietic and non-hematopoietic cells [Hernandez 2003]. The mutation in the CXCR4 receptor is known to prevent the normal release of mature neutrophils from the bone marrow to the blood [Kawai 2005] resulting in neutropenia in patients with WHIM syndrome [Dale 2011]. In addition to neutropenia, WHIM syndrome is characterized by lymphopenia that affects the levels of circulating T and B cells. [Balabanian 2012, Dotta 2011] resulting in low levels of immunoglobulins. The exact mechanism for lymphopenia is not known but may be attributable to interruption of the normal trafficking of lymphocytes and their retention in the marrow and other lymphoid tissues [Ma 1999].

Generally, clinical symptoms first appear in early childhood with recurrent bacterial infections due to low levels of white blood cells and antibodies [NORD 2015]. Common infections include otitis media, cellulitis, impetigo, abscess, bacterial pneumonia, sinusitis, and periodontitis. Affected individuals are particularly susceptible to human papillomavirus (HPV), which can cause widespread warts affecting the hands, feet, face, and trunk and are often recalcitrant [NORD 2015]. Mucosal and genital warts may also develop and these warts are associated with an increased risk of progressing to cervical carcinoma [NORD 2015]. Current treatments include G-CSF and intravenous immunoglobulin but these are non-specific, expensive, difficult to administer, and only partially effective [Kawai 2009].

Present treatments available for patients with WHIM syndrome are insufficient. There is a clear unmet need for agents that improve outcomes in the treatment of such patients.

BRIEF DESCRIPTION OF THE FIGURES

FIG. 9 illustrates dose-dependent increases (2-3×) in WBC counts in human subjects who were administered X4P-001.

DETAILED DESCRIPTION OF CERTAIN EMBODIMENTS OF THE INVENTION

Figure 1:
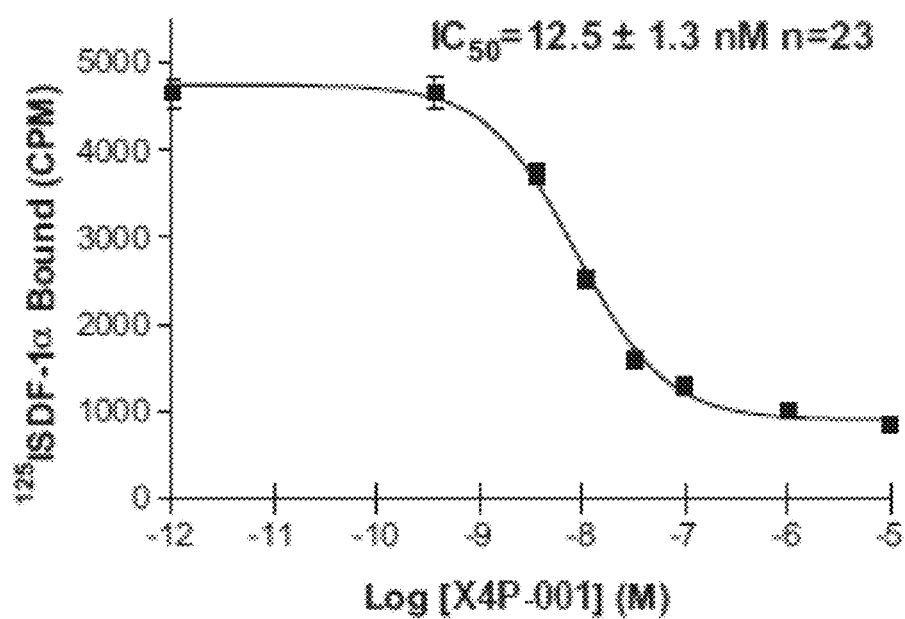
FIG. 1 illustrates X4P-001 inhibition on SDF-1α binding to CXCR4+CEM-CCRF cells.

Effective targeted treatments for WHIM syndrome, like X4P-001, are needed for the management of patients. X4P-001 can be administered orally, which in addition to being a targeted treatment, makes it an excellent candidate in a chronic treatment setting that would be required for patients with WHIM syndrome.

The ligand for the CXCR4 receptor is SDF-1α which is involved with numerous physiologic processes and plays a central role in hematopoieic cells homing to and being released from the bone marrow [Lapidot 2002]. Mutations in the CXCR4 prevent the normal release of mature neutrophils from the bone marrow into the blood [Kawai 2005]. Bone marrow examinations of patients affected with WHIM syndrome show abundant neutrophils with hyper-segmented nuclei and remnants of neutrophils in bone marrow macrophages. [Bohinjec 1981].

The disruption of the CXCR4/SDF-1α axis results in WHIM syndrome patients having low white blood cell counts usually <1.0×10$^9$/L with severe neutropenia and lymphopenia present [Dale 2011]. The mechanism of CXCR4/SDF-1α axis disruption is described in the following paragraph.

CXCR4 is a G protein-coupled receptor and engagement by SDF-1α induces typical activation of G protein—dependent pathways of a chemokine receptor [Baggiolini 1998, Zlotnik 2000]. These processes are regulated in a timely manner by the recruitment of β-arrestin to the receptor that precludes further G-protein activation (ie, desensitization) and leads to receptor internalization. Mutants of CXCR4 associated with WHIM syndrome give rise to impaired desensitization and internalization of the receptor upon SDF-1α exposure, leading to enhanced and prolonged receptor activation. [Hernandez 2003, Balabanian 2005, Gulino 2004, Kawai 2005, Lagane 2008, McCormick 2009]. Because CXCR4 normally regulates leukocyte trafficking and in particular is important for neutrophil adhesion in the bone marrow, prolonging the activity of SDF-1α dependent signaling is the probable cause for myelokathexis (MKX) and neutropenia seen in WHIM syndrome. [McDermott 2011-a].

X4P-001 is a small molecule antagonist of CXCR4 having the potential to block the enhanced signaling activity of mutant CXCR4 resulting in an increase in the number of circulating white blood cells by overcoming the impaired down regulation (receptor internalization) and receptor dysfunction caused by mutant CXCR4 (McDermott 2011-b). It has also been demonstrated that X4P-001 inhibits the most common genotypic forms of CXCR4 attributable to WHIM syndrome (R334X and E343X) to a similar extent as the wild type CXCR4 [Mosi 2012].

These studies demonstrated that oral administration of up to 400 mg BID for 3.5 days (healthy volunteers) and 200 mg BID for 8-10 days (healthy volunteers and HIV patients) was well-tolerated with no pattern of adverse events or clinically significant laboratory changes. These studies also demonstrated pharmacodynamic activity, with dose- and concentration-related changes in circulating white blood cells (WBCs); and a high volume of distribution (VL), suggesting high tissue penetration.

The inventors conceived that CXCR4 antagonism by X4P-001 may provide significant treatment benefits in patients with WHIMS, and individual aspects of WHIMS, which is an acronym for warts, hypogammaglobulinemia (low immunoglobulin levels), immunodeficiency (susceptibility to infections) and myelokathexis (trapping of white blood cells in the bone marrow). Administration of X4P-001 inhibits SDF-1α binding to CXCR4 and CXCR4+CEM-CCRF cells. [See FIG. 1]. Administration of X4P-001 also inhibits CXCR4 cell signaling and SDF-1α induced calcium flux. [See FIGS. 2-4]. In this manner, X4P-001 inhibits SDF-1α stimulated CCRF-CEM chemotaxis. [See FIG. 5].

Moreover, the inventors conceived that such a result might be achieved with comparatively little toxicity since CXCR4-targeted drugs are specifically targeted and do not induce cell cycle arrest in normal proliferating cell populations. Accordingly, the present invention provides significant advantages in treatment outcomes utilizing the low toxicity and effects of the CXCR4 inhibitor AMD11070 (X4P-001).

In the present invention, patients with WHIMS, or related syndromes, are treated with X4P-001, or a pharmaceutically acceptable salt or composition thereof either as a single agent (monotherapy), or in combination with another agent, such as granulocyte colony-stimulating factor (G-CSF), granulocyte-macrophage colony-stimulating factor (GM-CSF) or intravenous immunoglobulin (IVIG).

In some embodiments, the present invention provides a method for treating WHIMS in a patient in need thereof, wherein said method comprises administering to said patient X4P-001 or a pharmaceutically acceptable salt or composition thereof in combination with G-CSF, GM-CSF and/or IVIG. Other treatments that may be utilized in the treatment of WHIMS include bone marrow transplantation and treatment with cord blood stem cells.

In some embodiments, a provided method comprises administering the X4P-001, or a pharmaceutically acceptable salt or composition thereof, to a patient in a fasted state.

In certain embodiments, the present invention provides a method for treating WHIMS in a patient in need thereof, wherein said method comprises administering to said patient X4P-001, or a pharmaceutically acceptable salt or composition thereof, further comprising the step of obtaining a biological sample from the patient and measuring the amount of a disease-related biomarker. In some embodiments, the biological sample is a blood sample. In certain embodiments, the disease-related biomarker is selected from the group consisting of CXCR4, SDF-1α/CXCL12; and GRK3 (G protein coupled receptor kinase 3).

In certain embodiments, the present invention provides a method for treating WHIMS in a patient in need thereof, wherein said method comprises administering to said patient X4P-001 or a pharmaceutically acceptable salt or composition thereof.

In some embodiments, the X4P-001 or a pharmaceutically acceptable salt thereof is administered in a dose of from about 25 mg/day to about 150 mg/day.

In some embodiments, said patient exhibits warts.

In some embodiments, cells taken from the patient exhibit expression of a mutant form of CXCR4.

In some embodiments, cells taken from the patient exhibit increased expression of CXCR4.

In some embodiments, the method further comprises the step of obtaining a biological sample from the patient and measuring the amount of a disease-related biomarker.

In some embodiments, the biological sample is a blood sample.

In some embodiments, the disease-related biomarker is circulating CXCR4.

In some embodiments, the X4P-001 or a pharmaceutically acceptable salt or composition thereof is administered orally once per day.

In some embodiments, the X4P-001 or a pharmaceutically acceptable salt or composition thereof is administered orally twice per day.

In some embodiments, the present invention provides a unit dosage form comprising a composition comprising:
   (a) X4P-001, or a pharmaceutically acceptable salt thereof—about 10-20% by weight of the composition;
   (b) microcrystalline cellulose—about 70-85% by weight of the composition;
   (d) croscarmellose sodium—about 5-10% by weight of the composition;
   (e) sodium stearyl fumarate—about 0.5-2% by weight of the composition; and
   (f) colloidal silicon dioxide—about 0.1-1.0% by weight of the composition.

In some embodiments, the unit dosage form is in capsule form.

In some embodiments, the capsule comprises about 25 mg X4P-001, or a pharmaceutically acceptable salt thereof.

In some embodiments, the present invention provides a method for treating WHIM syndrome in a patient in need thereof, comprising the step of administering to the patient a disclosed unit dosage form.

In some embodiments, the present invention provides a method for treating WHIM syndrome in a patient in need thereof, comprising administering to said patient X4P-001 or a pharmaceutically acceptable salt or composition thereof, in an amount effective to increase absolute neutrophil count (ANC) and/or to increase absolute lymphocyte count (ALC) in the patient, for example in the patient's blood. In some embodiments, the ANC and/or ALC is increased in the patient to about 60%, 70%, 80%, 90%, 95%, or 100% of that of an average, healthy human who does not have WHIM syndrome or another immunodeficiency. In some embodiments, the ANC and/or ALC is increased in the patient to about 60%, 70%, 80%, 90%, 95%, or 100% of that of an average, healthy human of similar age, weight, and sex to that of the patient.

In some embodiments, the present invention provides a method for treating WHIM syndrome in a patient in need thereof, comprising administering to said patient X4P-001 or a pharmaceutically acceptable salt or composition thereof, in an amount effective to increase absolute neutrophil count (ANC) to a level greater than or equal to 600/μL and/or to increase absolute lymphocyte count (ALC) to a level greater than or equal to 1000/μL.

In some embodiments, said patient originally exhibited ANC less than 600/μL and/or ALC less than 1000/μL before treatment with X4P-001.

In some embodiments, said patient originally exhibited ANC less than 400/μL and/or ALC less than 650/μL before treatment with X4P-001.

In some embodiments, a disclosed method results in increases in ANC levels to at least about 600/μL, about 800/μL, about 1000/μL, about 1,200/μL, or to about that of a human with a normally-functioning immune system, on at least 85% of assessments.

In some embodiments, a disclosed method results in increases in ALC to at least about 1000/μL, about 1,200/μL, or about 1,500/μL, or to about that of a human with a normally-functioning immune system, on at least 85% of assessments.

In some embodiments, a disclosed method results in improved levels of protective antibody in the patient in response to a vaccine.

In some embodiments, a disclosed method results in a lowered frequency of infections in the patient, such as at least 50% less infections, such as respiratory tract infections.

In some embodiments, a disclosed method results in increased levels of total circulating WBC, neutrophils, and/or lymphocytes. In some embodiments, cell counts of WBC, neutrophils, and/or lymphocytes increase to at least 1.4× baseline. In some embodiments, cell counts of WBC, neutrophils, and/or lymphocytes increase to at least 1.8× baseline. In some embodiments, cell counts of WBC, neutrophils, and/or lymphocytes increase to at least 2.9× baseline. In some embodiments, cell counts of lymphocytes increase to at least 2.9× baseline. In some embodiments, cell counts of neutrophils increase to at least 2.7× baseline and lymphocytes to 1.9× baseline.

In some embodiments, the present invention provides a method of treating WHIMS in a patient in need thereof, wherein said method comprises administering to said patient an effective amount of X4P-001 or a pharmaceutically acceptable salt or composition thereof in conjunction with another treatment for warts, HPV infection, or neutropenia.

Dosage and Formulations

X4P-001 is a CXCR4 antagonist, with molecular formula $C_{21}H_{27}N_5$; molecular Weight 349.48 amu; appearance white to pale yellow solid; solubility: X4P-001 is freely soluble in the pH range 3.0 to 8.0 (>100 mg/mL), sparingly soluble at pH 9.0 (10.7 mg/mL) and slightly soluble at pH 10.0 (2.0 mg/mL). X4P-001 is only slightly soluble in water; and melting point of 108.9° ΔC.

The chemical structure of X4P-001 is depicted below.

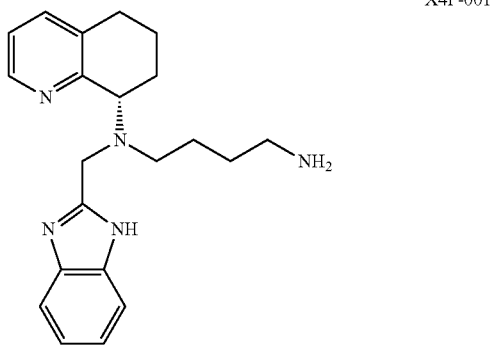

X4P-001

In certain embodiments, the composition containing X4P-001 is administered orally, in an amount from about 10 mg to about 600 mg daily. In certain embodiments, the dosage composition may be provided twice a day in divided dosage, approximately 12 hours apart. In other embodiments, the dosage composition may be provided once daily. The terminal half-life of X4P-001 has been generally determined to be between about 12 to about 24 hours, or approximately 14.5 hrs. Dosage for oral administration may be from about 10 mg to about 300 mg once or twice per day. In certain embodiments, the dosage of X4P-0001 useful in the invention is from about 20 mg to about 600 mg daily. In other embodiments, the dosage of X4P-001 useful in the invention may range from about 25 mg to about 200 mg daily, from about 25 mg to about 150 mg daily, from about 25 mg to about 100 mg daily, from about 25 mg to about 50 mg daily, from about 50 mg to about 150 mg daily, or from about 50 mg to about 100 mg daily.

In some embodiments, a provided method comprises administering to the patient a pharmaceutically acceptable composition comprising X4P-001 wherein the composition is formulated for oral administration. In certain embodiments, the composition is formulated for oral administration in the form of a tablet or a capsule. In some embodiments, the composition comprising X4P-001 is formulated for oral administration in the form of a capsule.

In certain embodiments, a provided method comprises administering to the patient one or more capsules comprising 10 mg to 1200 mg X4P-001 active ingredient; and one or more pharmaceutically acceptable excipients. In certain embodiments, the capsule is comprised of hard gelatin.

In certain embodiments, the present invention provides a composition comprising X4P-001, or a pharmaceutically acceptable salt thereof, one or more diluents, a disintegrant, a lubricant, a flow aid, and a wetting agent. In some embodiments, the present invention provides a composition comprising 10 mg to 1200 mg X4P-001, or a pharmaceutically acceptable salt thereof, microcrystalline cellulose, dibasic calcium phosphate dihydrate, croscarmellose sodium, sodium stearyl fumarate, colloidal silicon dioxide, and sodium lauryl sulfate. In some embodiments, the present invention provides a unit dosage form wherein said unit dosage form comprises a composition comprising 10-200 mg X4P-001, or a pharmaceutically acceptable salt thereof, microcrystalline cellulose, dibasic calcium phosphate dihydrate, croscarmellose sodium, sodium stearyl fumarate, colloidal silicon dioxide, and sodium lauryl sulfate. In certain embodiments, the present invention provides a unit dosage form comprising a composition comprising X4P-001, or a pharmaceutically acceptable salt thereof, present in an amount of about 10 mg, about 20 mg, about 25 mg, about 50 mg, about 75 mg, about 100 mg, about 150 mg, about 200 mg, about 250 mg, about 300 mg, about 400 mg, about 450 mg, about 500 mg, about 600 mg, about 700 mg, about 750 mg, about 800 mg, about 900 mg, about 1000 mg, about 1100 mg, or about 1200 mg. In some embodiments, a provided composition (or unit dosage form) is administered to the patient once per day, twice per day, three times per day, or four times per day. In some embodiments, a provided composition (or unit dosage form) is administered to the patient once per day or twice per day.

In some embodiments, the present invention provides a unit dosage form comprising a composition comprising:
(a) X4P-001, or a pharmaceutically acceptable salt thereof—about 10-30% by weight of the composition;
(b) microcrystalline cellulose—about 60-80% by weight of the composition;
(c) croscarmellose sodium—about 5-10% by weight of the composition;
(d) sodium stearyl fumarate—about 0.5-2% by weight of the composition; and (e) colloidal silicon dioxide—about 0.1-1.0% by weight of the composition.

In some embodiments, the present invention provides a unit dosage form comprising a composition comprising:
(a) X4P-001, or a pharmaceutically acceptable salt thereof—about 14.7% by weight of the composition;
(b) microcrystalline cellulose—about 78.1% by weight of the composition;
(c) croscarmellose sodium—about 6.0% by weight of the composition;
(d) sodium stearyl fumarate—about 1.0% by weight of the composition; and
(e) colloidal silicon dioxide—about 0.2% by weight of the composition.

In some embodiments, the present invention provides a unit dosage form comprising a composition comprising:
(a) X4P-001, or a pharmaceutically acceptable salt thereof—about 10-20% by weight of the composition;
(b) microcrystalline cellulose—about 25-40% by weight of the composition;
(c) dibasic calcium phosphate dihydrate—about 35-55% by weight of the composition;
(d) croscarmellose sodium—about 4-15% by weight of the composition;
(e) sodium stearyl fumarate—about 0.3-2% by weight of the composition;
(f) colloidal silicon dioxide—about 0.1-1.5% by weight of the composition; and
(g) sodium lauryl sulfate—about 0.1-1.5% by weight of the composition.

In some embodiments, the present invention provides a unit dosage form comprising a composition comprising:
(a) X4P-001, or a pharmaceutically acceptable salt thereof—about 12.85% by weight of the composition;
(b) microcrystalline cellulose—about 31.92% by weight of the composition;
(c) dibasic calcium phosphate dihydrate—about 44.4% by weight of the composition;
(d) croscarmellose sodium—about 8.33% by weight of the composition;
(e) sodium stearyl fumarate—about 1.38% by weight of the composition;
(f) colloidal silicon dioxide—about 0.42% by weight of the composition; and
(g) sodium lauryl sulfate—about 0.7% by weight of the composition.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for co-administration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

The contents of each document cited in the specification are herein incorporated by reference in their entireties.

EXEMPLIFICATION

Example 1: Non-Clinical Evaluation of X4P-001 Effects on CXCR4

In Vitro Pharmacology

The in-vitro pharmacology of X4P-001 (formally designated AMD11070) was extensively studied and the results reported [Mosi 2012]. Presented below is the relevant information from the Mosi 2012 literature publication. The SDF-1α isoform was used for the experiments described below.

X4P-001 Inhibition of SDF-1α Binding to CXCR4

Figure 2:
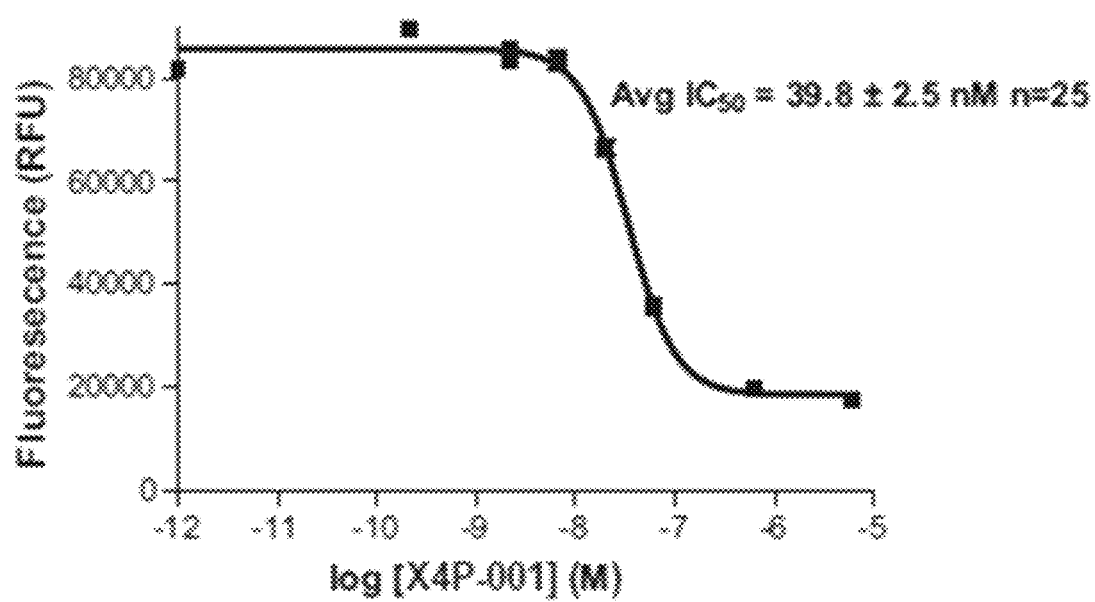
FIG. 2 illustrates X4P-001 inhibition of SDF-1α stimulated Eu-GTP binding.

X4P-001 was shown to inhibit binding of [$^{125}$I]-SDF-1α to CCRF-CEM cells (T-lymphoblastoid cell line which naturally express CXCR4 [Crump 1997]) in a heterologous competition binding assay. The results of the assay are shown in FIG. 2 below. The data was fitted to a single site binding model and gave an $IC_{50}$ of 12.5±1.3 nM.

X4P-001 Inhibition of CXCR4 Cell Signaling

Figure 3:
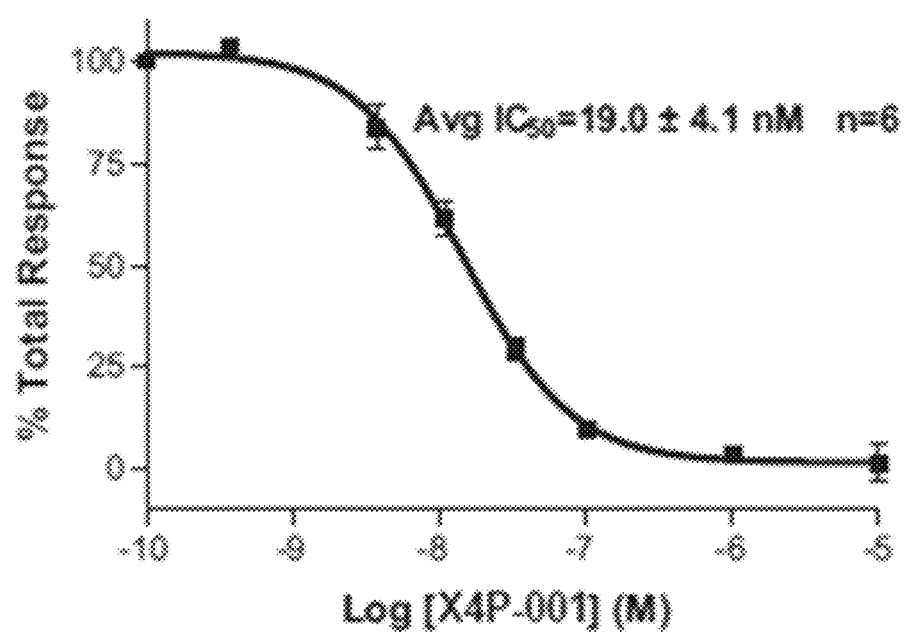
FIG. 3 illustrates X4P-001 inhibition of SDF-1α stimulated [$^{35}$S]-GTP-γ-S binding.
Figure 4:
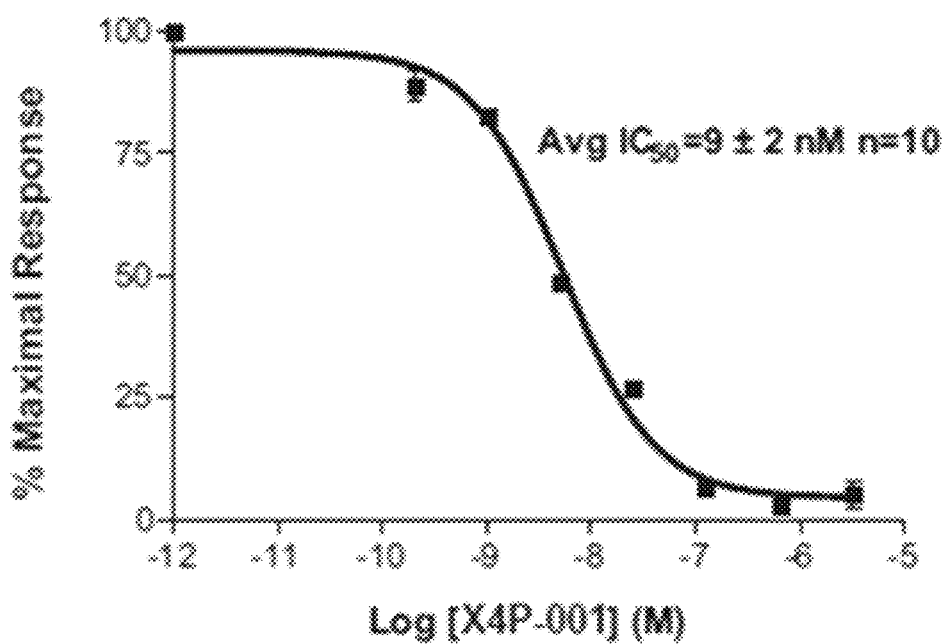
FIG. 4 illustrates X4P-001 inhibition of SDF-1α induced calcium flux.

CXCR4 is a G-protein coupled receptor [Baggiolini 1998, Zlotnik 2000]. As such the activation of the receptor can be measured using a nonhydrolysable analogue of GTP such as fluorescently labeled Europium-GTP (Eu-GTP) or radio labeled [$^{35}$S]-GTPγS. The results shown in FIG. 3 and FIG. 4 showed that X4P-001 inhibited CXCR4 activation with $IC_{50}$ values of 39.8±2.5 nM and 19.0±4.1 nM in the Eu-GTP binding and [$^{35}$S]-GTPγS assays, respectively.

Figure 5:
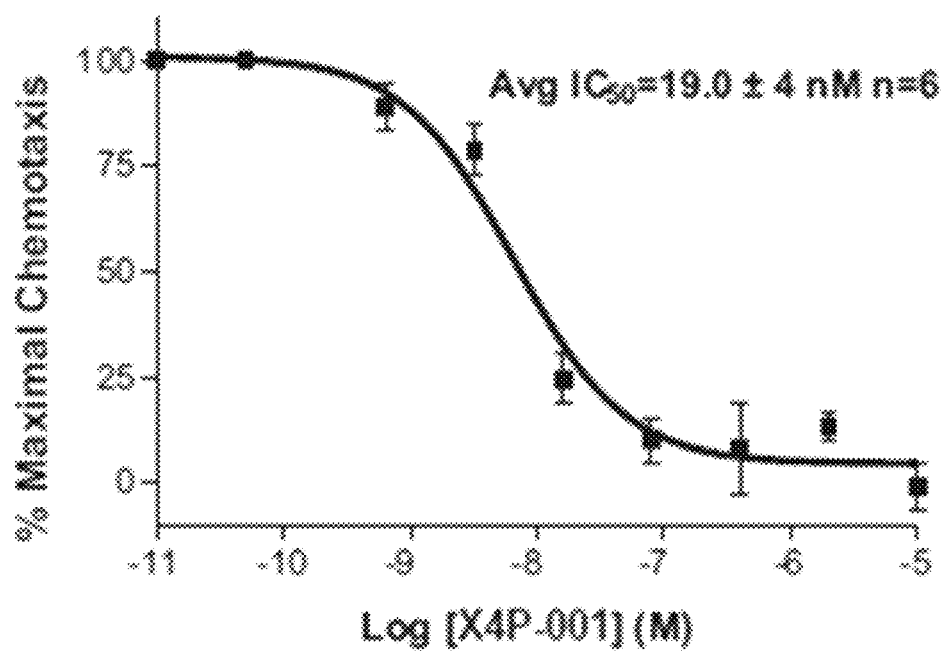
FIG. 5 illustrates X4P-001 inhibition of SDF-1α stimulated CCRF-CEM chemotaxis.

Upon activation of a G-protein coupled receptor, intracellular signaling pathways are triggered resulting in the release of calcium from intracellular stores. This calcium flux can be assayed using a calcium-chelating molecule, Fluo-4, which fluoresces upon binding calcium. X4P-001 was able to inhibit SDF-1α (2.5 nM SDF-1α) mediated calcium flux in CCRF-CEM cells with an $IC_{50}$ of 9.0±2.0 nM. The result is shown in FIG. 5.

Figure 6:
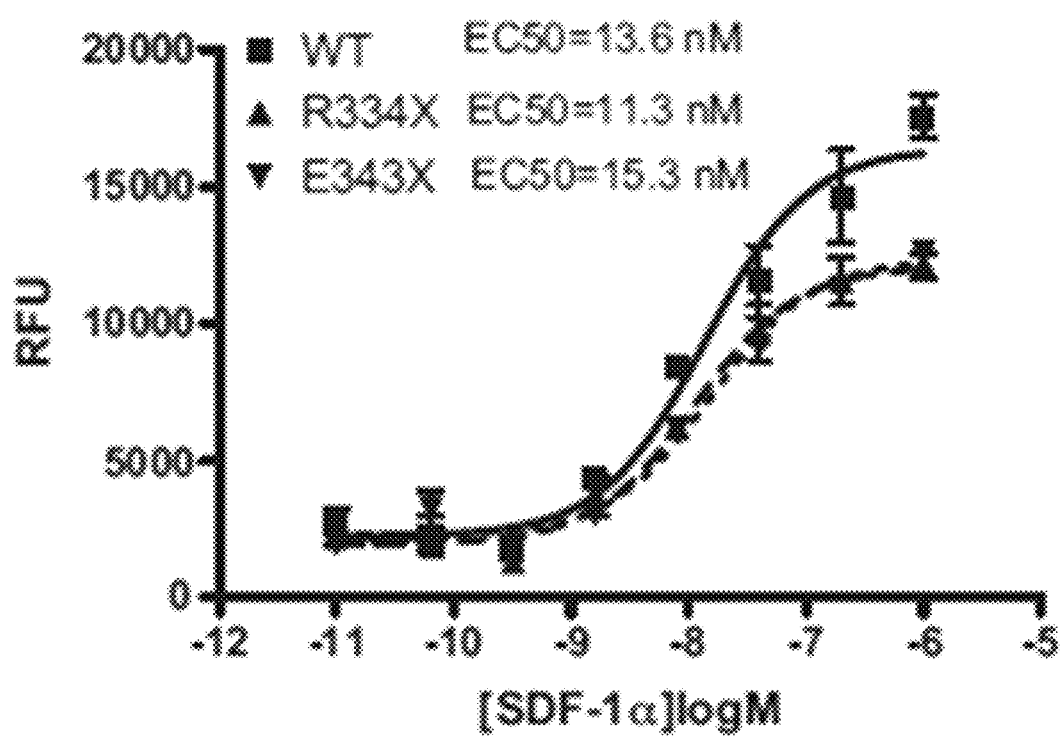
FIG. 6 illustrates SDF-1α stimulation of calcium flux in wild-type and CXCR4 variants.

A key property of all chemokines is that they induce a chemotactic response to a chemokine concentration gradient. X4P-001 was able to inhibit SDF-1α mediated chemotaxis of CCRF-CEM cells with an $IC_{50}$ of 19.0±4.0 nM as shown in FIG. 6.

A summary of the above in vitro results is presented in Table 1 below:

TABLE 1

In Vitro Concentrations of X4P-001($IC_{50}$) Associated with Different Biological Responses

| Response | $IC_{50}$ (nM)[a] |
|---|---|
| Ligand Binding | 12.5 ± 1.3 |
| Eu-GTP | 39.8 ± 2.5 |

TABLE 1-continued

In Vitro Concentrations of X4P-001(IC$_{50}$) Associated with Different Biological Responses

| Response | IC$_{50}$ (nM)$^a$ |
|---|---|
| [$^{35}$S]-GTP | 19.0 ± 4.1 |
| Calcium Flux | 9.0 ± 2.0 |
| Chemotaxis | 19.0 ± 4.0 |
| Average IC$_{50}$ | 21.5 |

$^a$ = Results are expressed as mean ± SE

X4P-001 Selectivity for CXCR4

In order to demonstrate the specificity of X4P-001 for CXCR4 it was tested in calcium signaling assays against a panel of chemokine receptors, and in ligand binding assays for BLT$_1$, the receptor for leukotriene B4 (LTB$_4$), and CXCR7. LTB$_4$ is a potent chemoattractant and its receptor is a G-protein coupled receptor. The results in Table 2 show that the IC$_{50}$ of X4P-001 against CCR1, CCR2b, CCR4, CCR5, CCR7, CXCR3, and LTB$_4$ was >50 mM in all cases. X4P-001 did not inhibit SDF-1α binding to CXCR7 at a concentration of 10 mM, the maximum concentration tested in this assay. Together these data indicate that X4P-001 is a selective inhibitor of CXCR4.

In order to demonstrate the specificity of X4P-001 for CXCR4 it was tested in calcium signaling assays against a panel of chemokine receptors, and in ligand binding assays for BLT$_1$, the receptor for leukotriene B4 (LTB$_4$), and CXCR7. LTB$_4$ is a potent chemoattractant and its receptor is a G-protein coupled receptor. The results in Table 2 show that the IC$_{50}$ of X4P-001 against CCR1, CCR2b, CCR4, CCR5, CCR7, CXCR3, and LTB$_4$ was >50 mM in all cases. X4P-001 did not inhibit SDF-1α binding to CXCR7 at a concentration of 10 mM, the maximum concentration tested in this assay. Together these data indicate that X4P-001 is a selective inhibitor of CXCR4.

TABLE 2

Calcium Flux Response for Cell Lines Treated with X4P-001 for IC$_{50}$ Determination

| Receptor | Cell line | Ligand | IC$_{50}$AMD11070 (µM) |
|---|---|---|---|
| CCR1 | HEK293F-CCR1 | MIP-1α/CCL3 | >50 |
| CCR2b | HEK293F-CCR2b | MCP-1/CCL2 | >50 |
| CXCR3 | HEK293F-CXCR3-Gαq15 | IP-10/CXCL10 | >50 |
| CXCR7 | Cf2Th.CXCR7 | SDF-1α/CXCL12 | >10 |
| CCR4 | HEK293F-CCR4-Gαq15 | TARC/CCL17 | >50 |
| CCR5 | HEK293F-CCR5 | RANTES/CCL5 | >50 |
| CCR7 | CCRF-CEM | MIP-3β/CCL19 | >50 |
| BLT$_1$ | CHO-S-LTB$_4$ | LTB$_4$ | >50 |

X4P-001 Inhibition of C-terminal Variants of CXCR4

Figure 7:
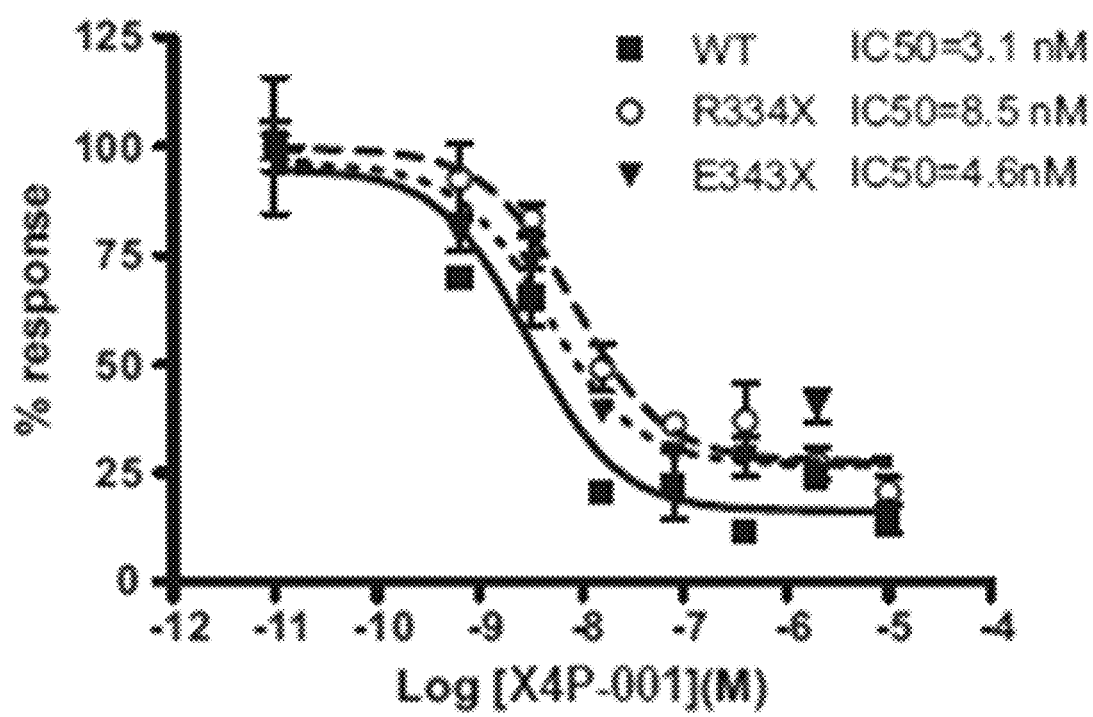
FIG. 7 illustrates X4P-001 inhibition of SDF-1α stimulation in wild-type and CXCR4 variants.

From a therapeutic perspective it is important that CXCR4 antagonists can act on CXCR4 variants. Carboxy-terminal truncated variants of CXCR4 have been reported associated with WHIM syndrome; nonsense mutations resulting in a 19 amino acid truncation (R334X), and a 10 amino acid truncation (E343X) and a frameshift mutation resulting in a 13 amino acid truncation (S339fs342X) [Hernandez 2003, Kawai 2009]. The R334X and E343X CXCR4 variants were cloned and transiently expressed in the canine thymus cell line Cf2Th. This cell line was chosen due to its lack of expression of CXCR4 [Wong 2008]. Wild type CXCR4 was similarly sub-cloned into this cell line for control studies. In control studies it was demonstrated that both these carboxy-terminal truncated variants were able to respond to SDF-1α in the calcium flux assay with a similar potency to wild type CXCR4. The EC$_{50}$ values for SDF-1α were 13.6, 11.3 and 15.3 nM against the wild type, R334X and E343X variants of CXCR4, respectively (FIG. 6). The inhibitory effect of X4P-001 on SDF-1α-mediated calcium flux was assessed for the two CXCR4 variants. Both variants were inhibited to a similar extent as the wild type CXCR4 with IC$_{50}$ values of 3.1, 8.5 and 4.6 nM for the wild type, R334X and E343X variants respectively (FIG. 7).

Discussion and Conclusions from In Vitro Studies

Using the CCRF-CEM cell line, which naturally expresses CXCR4 [Crump 1997] it was shown that X4P-001 inhibits SDF-1α ligand binding to CXCR4 with an IC$_{50}$ of 12.5±1.3 nM. X4P-001 also inhibited CXCR4 activation and signaling as shown by inhibition of SDF-1α mediated G-protein activation of the CXCR4 receptor in two assays using either the fluorescent Eu-GTP or the radiolabeled [$^{35}$S]-GTPγS binding assays with IC$_{50}$ values of 39.8±2.5 nM and 19.0±4.1 nM, respectively, and inhibition of SDF-1α mediated calcium flux with an IC$_{50}$ of 9.0±2.0 nM. X4P-001 also inhibited SDF-1α-mediated chemotaxis, a CXCR4-mediated physiological response, with an IC$_{50}$ of 19.0±4.0 nM. In addition, X4P-001 had little or no inhibitory effect on either MIP1α, MCP-1, TARC, RANTES, MIP-3β, or IP10 mediated calcium flux, ligands for CCR1, CCR2b, CCR4, CCR5, CCR7 and CXCR3, respectively, or SDF-1α binding to CXCR7, or LTB4 binding to BLT1, an alternative G-protein coupled receptor that mediates chemotaxis. These data indicate that X4P-001 is a selective inhibitor of CXCR4 over the other chemokine receptors evaluated.

Mutations in CXCR4 resulting in truncation of the intracellular carboxy-terminus of the receptor have been linked to the rare condition, WHIM syndrome [Hernandez 2003, Kawai 2009]. Two of these CXCR4 variants were evaluated and the results demonstrated that X4P-001 was able to inhibit SDF-1α-mediated calcium flux in these carboxy-terminal truncated variants. These data further indicate that X4P-001 acts via interaction with the extracellular region of CXCR4. Furthermore it is significant from the perspective of X4P-001 as a potential therapeutic option for WHIM syndrome that it can inhibit multiple variants of CXCR4.

Additionally it was shown that X4P-001 is an allosteric inhibitor of CXCR4 by comparing the dose/response of SDF-1α in the calcium flux assay in the presence of increasing amounts of X4P-001 [Mosi 2012]. Based on inhibition being mediated by non-competitive binding, the extent of inhibition is therefore dependent solely on the concentration of X4P-001 and is independent of the concentration of SDF-1α ligand.

In-Vivo Pharmacology

The primary in vivo pharmacologic effect of X4P-001 is mobilization of white blood cells (WBC) from bone marrow. Three studies are summarized below which demonstrate the mobilization of WBC from the bone marrow of beagle dogs and C3W/He J mice.

Hematologic Effects in the Male Beagle Dog

Three fasted male Beagle dogs received a single dose of X4P-001 in aqueous solution by oral gavage at dose levels of 5, 15, and 35 mg/kg (1 dog per dose level) in a volume of 1 mL/kg. Blood samples (approximately 3 mL each) were obtained at multiple timepoints from each animal by direct venipuncture of the jugular vein and collected using Vacutainer® tubes containing K$_3$EDTA as the anticoagulant. Blood samples were obtained at pre-dose, and 0.25, 0.5, 0.75, 1, 1.5, 2, 3, 4, 7, 12, and 24 hours post-dose. Blood samples were stored at ambient room temperature prior to automated differential analysis Body weights were determined prior to dosing on the day of test article administration. Animals were observed at least once daily and at times of blood sampling.

Hematology parameters included the following:
White Blood Cell Count (WBC)
Differential white blood cell count (absolute and relative)
Neutrophil
Lymphocytes
Monocytes
Eosinophils
Basophils
Large Unstained Cells (LUC)
Hematocrit (HCT)
Hemoglobin (HGB)
Mean Corpuscular Hemoglobin (MCH)
Mean Corpuscular Hemoglobin Concentration (MCHC)
Mean Corpuscular Volume (MCV)
Platelet Count (PLT)
Red Blood Cell Count (RBC)

Results

Figure 8:
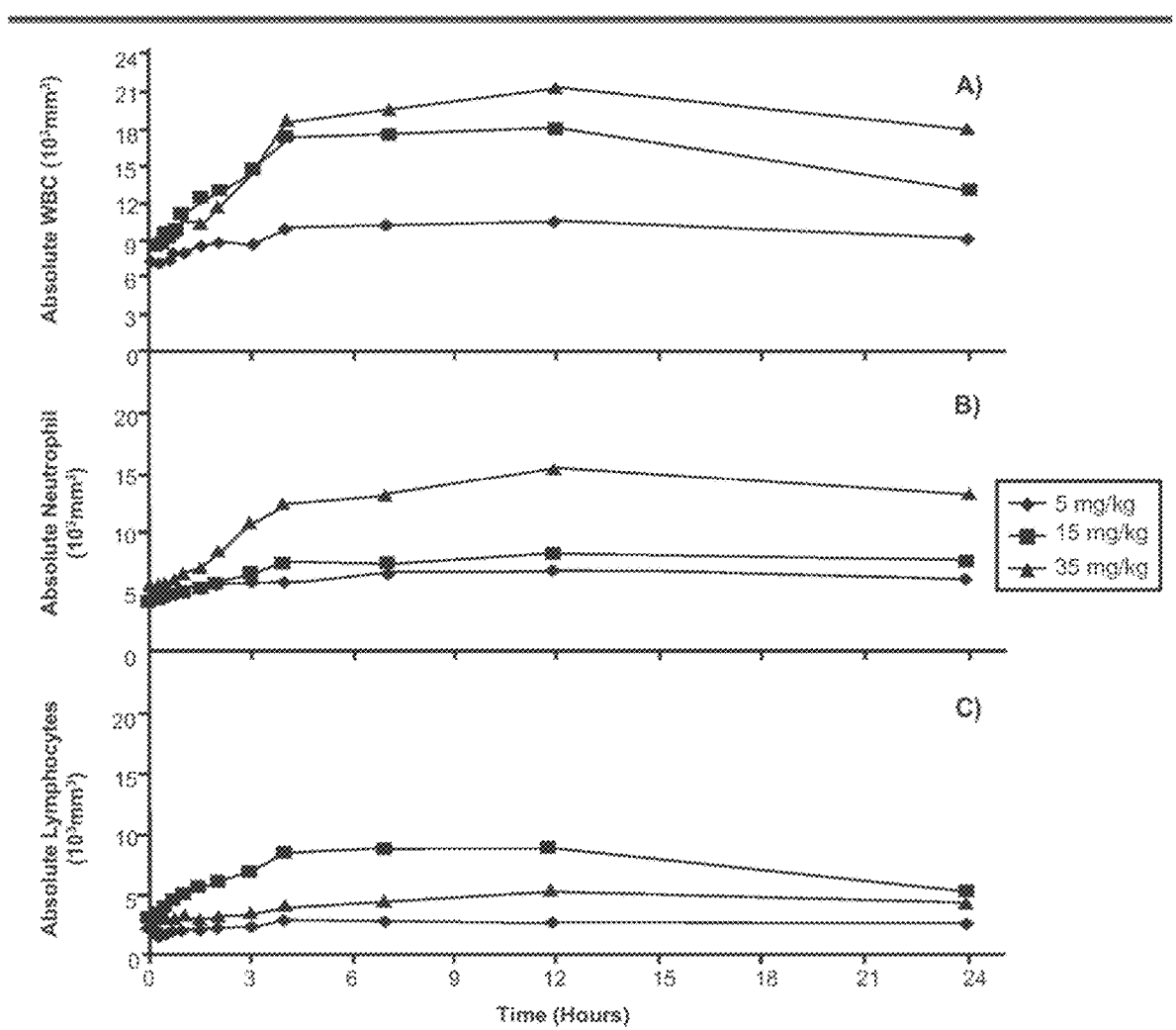
FIG. 8 illustrates white blood cell (A), neutrophil (B), and lymphocyte (C) counts following oral administration of X4P-001 to male beagle dogs.

The effect of X4P-001 on WBC and absolute neutrophil and lymphocyte counts is shown in FIG. 8. Maximal increases in WBC occurred 4-12 hours post-dose. Peak elevations ranged from 1.8-2.9-fold above baseline values at the 15 and 35 mg/kg dose levels, with somewhat lower (1.5-fold) elevations observed at the 5 mg/kg dose level. Although limited by the small sample size, these results suggest that maximal increases may have been achieved at the higher dose levels. WBC, neutrophil, and lymphocyte counts remained elevated at the 15 and 35 mg/kg dose levels at 24 hours, with evidence of return to baseline. No other hematological effects were observed.

A 28-Day Oral (Capsule) Study in the Beagle Dog with a 14-Day Recovery Period

A 28-Day GLP oral (capsule) toxicology study was conducted with X4P-001 in the male and female beagle dog, and hematology effects were observed, with X4P-001 administered twice-daily (at least 7 hours apart) by oral capsule for 28 days. A subset of treated animals was evaluated after a 14-day recovery period. Table 3 presents the protocol design and Table 4 the evaluations schedule.

TABLE 3

Protocol Design for 28-Day Toxicity Study in the Dog

| Group | Dose Level (mg/kg/day)[a] | Animals Terminal Necropsy | Animals 14-day Recovery |
|---|---|---|---|
| 1 | 0 (empty capsule) | 3 M, 3 F | 2 M, 2 F |
| 2 | 10 | 3 M, 3 F | — |
| 3 | 30 | 3 M, 3 F | — |

TABLE 4

Protocol Evaluations and Schedules

| Evaluations | Schedule |
|---|---|
| Study duration | Days −10 through Day 42 |
| Treatment | Days 1 through 28, twice daily |
| Clinical observation | Twice daily |
| Food consumption | Daily |
| Body weight | Weekly |

TABLE 4-continued

Protocol Evaluations and Schedules

| Evaluations | Schedule |
|---|---|
| Vital signs[a] | Predose acclimation period; final dosing week; final recovery week |
| Ophthalmology | Predose and during Week 4 |
| Electrocardiogram evaluation | Predose and during Week 4, at ~1 hour post-first daily dose |
| Clinical Pathology[b] | Predose d −10, d −2; Post-dose, Day 29 (all groups), Day 42 (recovery only) |
| Necropsy[c] | Day 29, terminal; Day 42, recovery |

[a]Vital signs comprise heart rate, blood pressure, and body temperature
[b]Clinical pathology comprised hematology, coagulation, serum, and urinalysis (done only once predose).
[c]Necropsy studies comprise organ weight, macroscopic, and microscopic observations, including 500-cell bone marrow differential count.

As shown in Table 5 below, increases in absolute counts for neutrophils, lymphocytes, and monocytes were observed at termination (Day 28); these were of greater magnitude and more likely statistically significant in females. These changes were considered consistent with the pharmacological effects of X4P-001. After the 14-day recovery period (only 100 mg/kg dose group evaluated) all hematology results returned to within normal levels.

TABLE 5

Hematology Findings at Termination in 28-Day Oral Toxicity Study in the Dog

| Observation | 10 mg/kg/d (3M, 3F) | 30 mg/kg/d (3M, 3F) | 100 mg/kg/d (3M, 3F) |
|---|---|---|---|
| Hematology neutrophils (abs) | M incr 1.2x; F incr 1.9x† | M incr 1.2x; F incr 2.3x† | M incr 1.8x; F incr 2.8x† |
| lymphocytes (abs) | M incr 1.3x; F incr 1.4x | M incr 1.6x; F incr 1.6x† | M incr 2.3x†; F incr 1.4x† |
| monocytes (abs) | M incr 1.2x; F incr 1.6x† | M incr 1.3x; F incr 1.9x† | M incr 1.9x†; F incr 2.4x† |
| reticulocytes | No changes | No changes | F decr 0.24x† |
| Coagulation | No changes | No changes | No changes | abs, absolute;
†p < 0.05 compared with control animals of the same sex

Hematologic Effects of X4P-001 in Mice

A further study was conducted to determine whether X4P-001 mobilizes progenitor/stem cells in mice. All experiments were performed in C3W/He J mice. X4P-001 and AMD3100/plerixafor were administered via single subcutaneous injection at the doses described below. The mobilization capacity of X4P-001 was assessed by the numbers of granulocyte-macrophage (CFU-GM), erythroid (BFU-E) and multipotential (CFU-GEMM) progenitor cells per mL of blood. The progenitors were stimulated to form colonies in vitro with the combination of 1 U/mL rhu EPO, 50 ng/mL rmu SLF, 5% vol/vol pokeweed mitogen mouse spleen cell conditioned medium (PWMSCM), and 0.1 mM hemin. Plates were scored 7 days after incubation at 37° C., 5% $CO_2$, lowered (5% $CO_2$) and in a humidified chamber.

Results

X4P-001 mobilized progenitors in C3H/HeJ mice following a single subcutaneous injection. In the first experiment (data shown in Table 6), mice received a dose of 5 mg/kg-and the number of progenitors in the circulating blood was measured at various time points (0.25, 0.5, 1, 2, 6 and 24 hours). The peak of nucleated cell mobilization occurred at approximately 1-2 hours post-injection. Peak increases of CFU-GM, BFU-E and CFU-GEMM were 4.21 (30 min.), 2.49-2.54 (30-60 min.), and 2.58-2.67 (30-60 min.)-fold, respectively over control (saline injection).

TABLE 6

X4P-001 Time Course of Progenitor Mobilization

| | | | AMD11070 Time Course (dose = 5 mg/kg) | | | | | |
|---|---|---|---|---|---|---|---|---|
| | | Control | @ - 15" | @ - 30" | @ - 60" | @ - 2' | @ - 6' | @ - 24' |
| Nucleated | Mean | 4.35 | 5.10 | 6.14 | 6.92 | 8.29 | 5.66 | 4.31 |
| Cellularity | STD | 0.14 | 1.09 | 1.20 | 0.57 | 0.55 | 0.28 | 0.82 |
| ($\times 10^6$/mL) | STE | 0.08 | 0.63 | 0.69 | 0.33 | 0.32 | 0.16 | 0.47 |
| PBL-LD | Fold Chg | 1.00 | 1.17 | 1.41 | 1.59 | 1.90 | 1.30 | 0.99 |
| | P | 1.000 | 0.307 | 0.062 | 0.002 | 0.000 | 0.002 | 0.930 |
| GM | Mean | 302.3 | 785.1 | 1273.8 | 866.0 | 897.5 | 387.5 | 386.3 |
| | STD | 20.5 | 180.3 | 85.4 | 197.8 | 165.6 | 54.6 | 110.5 |
| | STE | 11.8 | 104.1 | 49.3 | 114.2 | 95.6 | 31.5 | 63.8 |
| | Fold Chg | 1.00 | 2.60 | 4.21 | 2.86 | 2.97 | 1.28 | 1.28 |
| | P | 1.000 | 0.010 | 0.000 | 0.008 | 0.003 | 0.065 | 0.265 |
| BFU | Mean | 92.5 | 148.8 | 230.4 | 235.1 | 165.3 | 99.9 | 84.6 |
| | STD | 30.9 | 27.1 | 70.2 | 68.2 | 47.5 | 17.8 | 44.4 |
| | STE | 17.8 | 15.6 | 40.5 | 39.4 | 27.4 | 10.3 | 25.7 |
| | Fold Chg | 1.00 | 1.61 | 2.49 | 2.54 | 1.79 | 1.08 | 0.92 |
| | P | 1.000 | 0.076 | 0.036 | 0.030 | 0.090 | 0.735 | 0.814 |
| GEMM | Mean | 38.6 | 65.6 | 99.6 | 103.1 | 68.9 | 37.6 | 37.7 |
| | STD | 10.6 | 17.6 | 24.2 | 20.3 | 23.7 | 16.0 | 20.6 |
| | STE | 6.1 | 10.2 | 14.0 | 11.7 | 13.7 | 9.3 | 11.9 |
| | Fold Chg | 1.00 | 1.70 | 2.58 | 2.67 | 1.78 | 0.97 | 0.98 |
| | P | 1.000 | 0.085 | 0.016 | 0.008 | 0.114 | 0.934 | 0.946 |

Animals per group = 3, control group = 1, total animals = 21

An X4P-001 dose-response was performed by measurement of the number of circulating progenitors in the blood at 1 hour post-injection at various doses (1.5, 2.5, 5, 10 and 20 mg/kg). As shown in Table 7, there appears to be an upper limit to the number of progenitors that can be mobilized with X4P-001, exemplified by the fold increases of CFU-GM. The numbers of CFU-GM in the circulating blood dose-dependently increased with peak fold increase of 6.0-7.7 over control at 5-20 mg/kg. Peak fold increases respectively of 2.3 and 3.8 for BFU-E and CFU-GEMM were noted at 10 mg/kg. At doses below 5 mg/kg X4P-001, the fold-increases in the numbers of BFU-E and CFU-GEMM were not statistically significant.

A final experiment was performed to compare the progenitor cell mobilization capacity of X4P-001 and AMD3100/plerixafor. Both drugs were administered subcutaneously at a dose of 5 mg/kg, and the number of progenitors in the circulating blood were measured for AMD3100 at a single 1 hour time point (the peak of mobilization with AMD3100, data not shown) versus X4P-001 at 0.25, 0.5, 1 and 2 hours post-injection. As shown in Table 8 comparing the fold-increase in CFU-GM, BFU-E, and CFU-GEMM, AMD3100 caused respective maximum increases of 9.11, 3.12, and 4.35, whereas respective peaks of mobilization with X4P-001 were 3.56, 2.84 and 3.21.

TABLE 7

Dose Response in C3H/HeJ Mice

| | | | AMD11070 (mg/kg) | | | | |
|---|---|---|---|---|---|---|---|
| | | Control | 20 | 10 | 5 | 2.5 | 1.5 |
| Nucleated | Mean | 6.48 | 9.62 | 9.94 | 7.65 | 8.29 | 6.94 |
| Cellularity | STD | 0.69 | 1.26 | 4.02 | 2.74 | 2.07 | 0.50 |
| ($\times 10^6$/mL) | STE | 0.40 | 0.73 | 2.32 | 1.58 | 1.20 | 0.29 |
| PBL-LD | Fold Chg | 1.00 | 1.48 | 1.53 | 1.18 | 1.28 | 1.07 |
| | P | 1.000 | 0.019 | 0.216 | 0.514 | 0.225 | 0.406 |
| GM | Mean | 188.0 | 1314.2 | 1444.2 | 1119.8 | 626.5 | 428.0 |
| | STD | 51.8 | 262.0 | 939.8 | 1011.9 | 220.4 | 118.7 |
| | STE | 29.9 | 151.2 | 542.6 | 584.2 | 127.3 | 68.5 |
| | Fold Chg | 1.0 | 7.0 | 7.7 | 6.0 | 3.3 | 2.3 |
| | P | 1.000 | 0.002 | 0.082 | 0.186 | 0.028 | 0.033 |
| BFU | Mean | 114.4 | 261.4 | 268.1 | 181.6 | 144.8 | 143.8 |
| | STD | 5.6 | 35.8 | 61.4 | 58.6 | 79.3 | 47.1 |
| | STE | 3.2 | 20.7 | 35.5 | 33.8 | 45.8 | 27.2 |
| | Fold Chg | 1.0 | 2.3 | 2.3 | 1.6 | 1.3 | 1.3 |
| | P | 1.000 | 0.002 | 0.012 | 0.119 | 0.544 | 0.343 |
| GEMM | Mean | 58.4 | 145.0 | 224.4 | 141.0 | 78.3 | 53.3 |
| | STD | 45.5 | 50.5 | 60.7 | 34.4 | 8.1 | 8.9 |
| | STE | 26.3 | 29.2 | 35.0 | 19.8 | 4.7 | 5.1 |
| | Fold Chg | 1.0 | 2.5 | 3.8 | 2.4 | 1.3 | 0.9 |
| | P | 1.000 | 0.092 | 0.019 | 0.066 | 0.498 | 0.857 |

Animals per group = 3, control group 1, total animals = 18

TABLE 8

X4P-001 Time Course Compared to ADM3100/Plerixafor (Dose 5 mg/kg)

| | | Control | AMD3100 @ - 60" | AMD11070 @ - 15" | @- 30" | @ - 60" | @ - 2' |
|---|---|---|---|---|---|---|---|
| Nucleated Cellularity (×10⁶/mL) PBL-LD | Mean | 6.23 | 10.08 | 8.04 | 8.28 | 7.34 | 9.71 |
| | STD | 2.16 | 2.13 | 1.30 | 0.94 | 0.69 | 1.29 |
| | STE | 1.25 | 1.23 | 0.75 | 0.54 | 0.40 | 0.74 |
| | Fold Chg | 1.00 | 1.62 | 1.29 | 1.33 | 1.18 | 1.56 |
| | P | 1.000 | 0.092 | 0.281 | 0.205 | 0.444 | 0.074 |
| GM | Mean | 214.1 | 1950.3 | 588.3 | 705.9 | 761.4 | 619.6 |
| | STD | 118.2 | 566.4 | 168.1 | 151.5 | 239.2 | 158.7 |
| | STE | 68.2 | 327.0 | 97.1 | 87.5 | 138.1 | 91.6 |
| | Fold Chg | 1.00 | 9.11 | 2.75 | 3.30 | 3.56 | 2.89 |
| | P | 1.000 | 0.007 | 0.034 | 0.011 | 0.024 | 0.024 |
| BFU | Mean | 66.5 | 207.7 | 188.9 | 151.9 | 144.3 | 108.5 |
| | STD | 39.6 | 35.4 | 55.0 | 23.8 | 47.5 | 43.0 |
| | STE | 22.9 | 20.4 | 31.7 | 13.8 | 27.4 | 24.8 |
| | Fold Chg | 1.00 | 3.12 | 2.84 | 2.29 | 2.17 | 1.63 |
| | P | 1.000 | 0.010 | 0.035 | 0.033 | 0.095 | 0.281 |
| GEMM | Mean | 31.8 | 138.5 | 93.8 | 79.0 | 102.2 | 62.4 |
| | STD | 2.6 | 18.1 | 21.1 | 34.5 | 50.5 | 34.9 |
| | STE | 1.5 | 10.5 | 12.2 | 19.9 | 29.1 | 20.1 |
| | Fold Chg | 1.00 | 4.35 | 2.95 | 2.48 | 3.21 | 1.96 |
| | P | 1.000 | 0.001 | 0.007 | 0.078 | 0.074 | 0.205 |

Animals per group = 3, control group = 1, total animals =18

Conclusions from In Vivo Studies

Single oral doses of X4P-001 at 5, 15, and 35 mg/kg in beagle dogs resulted in increased levels of total circulating WBC, neutrophils, and lymphocytes. The increases were consistently apparent at 4 hours and typically peaked at 12 hour, occasionally earlier. At 5 mg/kg, all three cell counts increased to 1.47× baseline. At 15 mg/kg, neutrophils increased to 1.8× and lymphocytes to 2.9×; and at 35 mg/kg, neutrophils to 2.7× and lymphocytes to 1.9×.

In multiple-dose toxicity studies in dogs, hematological effects after 28 days were qualitatively and quantitatively consistent with the findings in the single dose study in beagle dogs.

In C3H/HeJ mice, X4P-001 dose-dependently increased the number of circulating progenitors up to a dose of 5-10 mg/kg s.c.

Example 2: Clinical: Patients to be Treated

Patients who may be treated according to the present invention include patients who have been diagnosed with WHIMS or with MKX; and patients who present the characteristic mutations in their CXCR4 gene. Other patients who may benefit from the present invention may include individuals presenting with the following screening criteria:

Neutropenia (ANC≤400 or ≤600/μL) and/or lymphopenia (ALC≤650 or ≤1000/μL)—the latter is not characteristic of other chronic neutropenias;

Neutropenia and chronic warts;

Myelokathexis on bone marrow aspirate;

Patients meeting the above criteria are genetically screened for MKX. Patients with the characteristic mutations in CXCR4 are the most likely to benefit from treatment in accordance with the present invention.

Thus, the effects of X4P-001 is expected to be greatest in patients with myelokathexis associated with mutation in CXCR4. In addition, patients who may benefit from treatment according to the present invention include individuals presenting with the following screening criteria:

1. Has a genotype-confirmed CXCR4 mutation consistent with WHIM syndrome; and
2. Has ANC≤400 or ≤600/μL, or ALC≤650 or ≤1000/μL, or both, on at least two independent blood samples collected over a period of up to 14 days.
3. Have one of the following findings:
    A bone marrow aspirate or biopsy showing myelokathexis
    Peripheral WBC counts (≥2 independent samples, obtained in the absence of signs or symptoms of acute infection, and when not having received G- or GM-CSF in the past 7 days) showing absolute neutrophil count <900/μL and/or absolute lymphocyte count <1,500/μL.

Examples of candidate endpoints based on 6 months on-treatment compared to the prior 6 months without treatment include:

50% reduction in hospitalizations

50% reduction in infections requiring courses of systemic antibiotics

50% reduction in area involving cutaneous warts sustained increases in circulating neutrophils (e.g., ANC>600/μL; ANC>800/μL; ANC>1000/μL; or ANC>1,200/μL on at least 85% of assessments)

sustained increases in circulating lymphocytes (e.g., ALC>1000/μL; ALC>1,200/μL; or ALC>1,500/μL on at least 85% of assessments)

Achieve pre-defined levels of protective antibody in response to at least 2 approved vaccines previously administered without achieving that level.

50% reduction in days of work or school missed due to infection sustained increases in circulating neutrophils.

Not all endpoints are applicable to all patients, just as all patients with WHIM do not exhibit identical clinical manifestations. However, all patients exhibit at least one clinical and one laboratory metric.

Patients are preferably initiated on treatment orally with X4P-001 25 mg once daily, 25 mg twice daily, or 50 mg once daily. Provision is made for dose reduction (which can be via increased interval; e.g., to every other day or twice weekly) in the event of toxicity or dose increase (e.g., to >50 mg once daily or higher daily dosage, such as 100 mg/day or 150 mg/day) in the event of an inadequate response.

An exemplary initial dosage is via X4P-001 25 mg capsules, administered orally in the morning in a fasted state, with no food or drink (except water) after midnight and continuing until 2 hr post-dose. In twice daily dosage regimens, capsules are preferably administered orally twelve hours apart.

Example 3: Clinical Treatment Regimens

Dosing Regimen for Patients with WHIM Syndrome:
X4P-001 at a determined dose of 25 mg or 50 mg daily is administered orally. Patients are instructed about both dosing schedule and requirements relating to food or drink near the time of dosing.

Dosing Schedule.
The first daily dose is taken in the morning. For twice daily dosing, doses should be taken twelve hours apart. Dosing should be at the same times each day±2 hr.

Restrictions relating to food. Absorption is impacted by food and patients will be instructed as follows:

For the morning dose:
No food or drink (except water) after midnight until the time of dosing
No food or drink (except water) for 2 hour after dosing.

Dosing of X4P-001 may be adjusted by the clinician as appropriate. The dose of X4P-001 may be lowered according to the judgment of the clinician. If a patient receiving X4P-001 experiences an adverse event at Grade >2, the dose of X4P-001 may be lowered according to the judgment of the clinician. If a patient successfully completes the first 2 to 4 weeks of treatment, that is, without experiencing any adverse events greater than Grade 2, the daily dose of X4P-001 may be increased consistent with the judgment of the clinician.

Alternative Dosing Regimens for Patients with WHIM Syndrome

Patients' initial absolute neutrophil count (ANC) (neutropenia) (ANC<400 or <600/μL) and/or absolute lymphocyte count (ALC) (lymphopenia) (ALC<650 or <1000/μL)] are measured. [Note—the latter is not characteristic of other chronic neutropenias]. If the patient exhibits ANC below 400 or below 600/μL; and/or ALC remains below 650 or below 1000/μL, then treatment with X4P-001 is initiated. Patients are initiated on treatment with X4P-001 25 mg orally once daily, 25 mg orally twice daily, or 50 mg orally once daily. Provision is made for dose reduction (which can be via increased interval, e.g., to every other day or twice weekly) or halt of administration in the event of toxicity, or dose increase (e.g., to >50 mg daily or higher daily dosage) in the event of an inadequate response.

ANC and ALC are monitored monthly or, preferably, bi-weekly. If ANC>400 or >600/μL; and/or ALC>650 or >1000/μL is achieved, the patient will continue on the original daily dosage regimen. If ANC remains below 400 or below 600/μL; and/or ALC remains below 650 or below 1000/μL, and the patient exhibits no severe adverse effects, the patient's dose will be increased to by 25 mg or 50 mg daily [or by 25 mg orally twice daily; 12 hours apart].

Patients on the increased dose of 50 mg/μL per day will continue to be monitored monthly or, preferably, bi-weekly. If ANC≥400 or ≥600/μL; ALC≥650 or ≥1000/μL is achieved (without severe adverse effects), the patient will continue on the increased dosage regimen. If ANC remains below 400 or below 600/μL; and/or ALC remains below 650 or below 1000/μL, (and patient exhibits no severe adverse effects), the patient's dose will be further increased to by an additional 25 mg or 50 mg daily.

The above procedures of increasing daily dosage regimens may be repeated until the patient achieves ANC≥400 or ≥600/μL; and/or ALC≥650 or ≥1000/μL (without severe adverse effects); or until the patient is being treated at a maximum tolerated daily dose.

Alternatively, ANC and ALC are analyzed as area-under-the-curve (AUC) relative to pre-specified clinically meaningful thresholds of 400 or 600/μL and 650 or 1000/μL, respectively. The 24-hour AUC will be calculated using the trapezoidal method with area above threshold being positive, and area below threshold, negative. Patients with $AUC_{ANC}$<2000 cell·hr/μL or $AUC_{ALC}$<5000 cell·hr/μL at monthly or bi-weekly evaluations will have X4P-001 daily dose increased in 25 mg or 50 mg increments up to a maximum dose of 150 mg QD. Because ANC and ALC in WHIM patients are significantly impacted by acute infection, alone or with antibiotic, G-CSF or IVIG treatment, monitoring of AUC should be delayed or discontinued in patients with acute infection, until such patient has remained afebrile for at least 2 weeks.

If the patient experiences adverse effects at any time, provision is made for dose reduction (i.e., lower dosage and/or increased interval between administrations drug), or administration is halted. Additionally, the treating physician may use his or her professional judgment and discretion in determining the starting dose, and how best to titrate to the appropriate dose of X4P-001 for any individual patient.

An exemplary composition of a X4P-001 25 mg capsule that may be used is shown in Table 9 below.

TABLE 9

Quantitative Composition of Exemplary X4P-001 25 mg Capsule

| Component | Reference to Standard | Function | Quantity (mg/capsule) | % w/w |
|---|---|---|---|---|
| X4P-001 | In House | Active Ingredient | 25.0 | 14.7 |
| Microcrystalline Cellulose | NF | Diluent | 132.7 | 78.1 |
| Croscarmellose Sodium | NF | Disintegrant | 10.2 | 6.0 |
| Sodium Stearyl Fumarate | NF | Lubricant | 1.7 | 1.0 |
| Colloidal Silicon Dioxide | USP | Flow Aid | 0.4 | 0.2 |
| Sum Total | | | 170.0 | 100.0 |
| Hard Gelatin Capsules, Size 1 | USP | Packaging | NA | NA |

Example 4: Assessments of Treatment Effect

Circulating White Blood Cells
Whole blood samples are analyzed for:
CBC and absolute leukocyte differential counts by standard laboratory methods, including WBC counts, including absolute numbers of lymphocytes, neutrophils, and CD34+ cells. The number and percentage of patients achieving ANC>1,500/μL; ALC>900/μL. The absolute increase in blood neutrophil counts from pre-treatment baseline for each subject, including at the maximum observed in the hours post-dosing; and the maximum observed pre-dose on stable drug administration regimen. These results are compared with data from healthy adults administered X4P-001.

Peripheral Blood Mononuclear Cells (PBMC) subpopulations by flow cytometry are shown below in Table 10.

TABLE 10

Candidate Subsets of Circulating Lymphocytes and Monocytes

| | | |
|---|---|---|
| CD4+ T cells | CD3− CD56+ (NK cells) | CD34+ (stem cells) |
| CD4+ CD45RA+ (naïve T cells) | CD19+ (B cells) | CD49f+ (stem cells) |
| CD4+ CD45RA− (memory T cells) | CD19+ CD27− IgM+ (transitional B cells) | CD90+ (stem cells) |
| CD8+ T cells | CD14+ (monocytes) | |
| CD8+ CD45RA+ (naïve T cells) | CD14+ CD16− (classical monocytes) | |
| CD8+ CD45RA− (memory T cells) | CD14+ CD16+ (inflammatory monocytes) | |

Immunoglobulins and Specific Antibodies

Serum samples are analyzed for levels of total IgG, IgG subclasses, IgA, and IgM, and levels of selected specific antibodies to common vaccine antigens (Table 11).

TABLE 11

Common Vaccines Which Elicit Protective Antibody by Age Range Initially Administered

| Birth to 6 years (bacteria) | Birth to 6 years (viruses) | Age 7 to 18 years |
|---|---|---|
| Diphtheria toxoid | Measles, Rubella | Meningococcal polysaccharide |
| Tetanus toxoid | Varicella Polio (inactivated vaccine) | Human papilloma virus |
| H. influenzae type B polysaccharide | Hepatitis B, Hepatitis A | |
| Pneumococcal polysaccharides | | |

The following parameters are reviewed:
Increases in levels of IgG, IgA, and IgM
For patients with sub-protective titers of specific antibody to approved microbial vaccines, the clinician and patient may decide upon revaccination, and analyze for development of protective titers post-vaccination.

Bone Marrow Aspirates

Bone marrow aspirates are obtained from consenting patients at screening, after 4 and after 20 weeks of treatment. Aspirates are reviewed by a blinded hematopathologist and graded for cellularity and myelokathexis. If sufficient material is available, samples are analyzed for markers of neutrophil apoptosis and lymphocyte subpopulations.

The following parameters are reviewed:
Decrease in hypercellularity
Decrease in fraction of apoptotic WBC
Clinical Assessments
Warts.
Warts are monitored by photographs and/or recording of lesion location, number, and size.

Infections.
Temperatures are taken twice daily, signs or symptoms of infections, resulting in fever, prompting physician visits, requiring antibiotics, or associated with hospitalization, are reviewed and compared with the year prior to treatment.

Pharmacokinetic Assessments

If desired, pharmacokinetic assessment of blood samples for plasma levels of X4P-001 may be conducted. Blood samples are collected as scheduled. Samples are analyzed for X4P-001 concentration using reversed-phase high performance liquid chromatography (RP-HPLC) with MS/MS detection. The validated range of this bioanalytic method is 30 to 3,000 ng/mL in plasma.

Pharmacokinetics (PK) and Pharmacodynamics (PD).

In order to evaluate the pharmacokinetic properties of therapy with X4P-001, levels of X4P-001, PK samples are obtained on all patients in Part A as follows
Day 1: pre-dose; post-dose at 30, 60, 90 min (each ±10%) and 2, 3, 4 hr (each ±15 min)
Week 5 visit: pre-dose; post-dose at 30, 60, 90 min (each ±10%) and 2, 3, 4, 8 hr (each ±15 min)
Week 9 and Week 13 visits: pre-dose.
Visits are scheduled for early in the day and patients are instructed to arrive at the clinic fasting and having not taken their morning dose of X4P-001.

PK are analyzed by patient and dosage regimen over the preceding week using descriptive statistics for AUC, Cmax, and Cmin.

If results suggest either (a) ongoing accumulation beyond Week 5 or (b) a specific PK parameter is associated with adverse effects, then additional sampling days may be added.

PD samples are collected on Day 1 and at Week 5 visit concurrent with scheduled PK samples (see above) for:
Total white blood cell (WBC) counts
Counts of circulating CD34+ positive cells
Assessments may include samples analyzed by flow cytometry for subpopulations of PBMCs.
If sample yields permit, additional investigational immunomodulatory subsets may be analyzed (See Table 11).

Of course, the treating physician may apply his or her professional judgment and discretion and any established standards of care, what parameters of assessment (e.g., the desired levels of ANC and ALC) should be used in determining the treatment regimen for any individual patient.

REFERENCES

Baggiolini; 1998. Chemokines and leukocyte traffic. *Nature.* 392: 565-568. Balabanian, et al. 2005. WHIM syndromes with different genetic anomalies are accounted for by impaired CXCR4 desensitization to CXCL12. *Blood.* 105:2449-2457.

Balabanian, et al. 2012. Proper desensitization of CXCR4 is required for lymphocyte development and peripherial compartmentalization in mice. *Blood.* 119: 5722-5730.

Beaussant-Cohen, et al.; Description and outcome of a cohort of 8 patients with WHIM syndrome from the French Severe Chronic Neutropenia Registry. *Orphanet J Rare Dis.* 2012; 7:71.

Bohinjec, 1981. Myelokathexis: chronic neutropenia with hyperplastic bone marrow and hypersegmented neutrophils in two siblings. *Blut.* 42:191-196.

Broxmeyer. A WHIM satisfactorily addressed. *Blood.* 2014; 123:2286-8.

Cao, et al.; Effect of Low-Dose Ritonavir on the Pharmacokinetics of the CXCR4 Antagonist AMD070 in Healthy Volunteers. *Antimicrob Agents Chemother.* 2008; 52:1630-1634.

Crump, et al. 1997. Solution structure and basis for functional activity of stromal cell derived factor-1; dissociation of CXCR4 activation from binding and inhibition of HIV-1. *EMBO J.* 16:6996-7007

Dale, et al. The CXCR4 antagonist plerixafor is a potential therapy for myelokathexis, WHIM syndrome. *Blood* 2011; 118:4963-4966.

Dale, et al., The Severe Chronic Neutropenia International Registry: 10-Year Follow-up Report. *Support Cancer Ther.* 2006; 3:220-31.

Doranz 1997. Chemokine receptors as fusion cofactors for human immunodeficiency virus type 1 (HIV-1). *Immunol Res.* 16:15-28.

Dotta, 2011. Clinical and genetic features of warts, hypogammaglobulinemia, infections and myelokathexis (WHIM) syndrome. Current Molecular Medicine; 11:317-325. Galsky, et al. 2014. A Phase I Trial of LY2510924, a CXCR4 Peptide Antagonist, in Patients with Advanced Cancer. *Clin Cancer Res.* doi: 10.1158/1078-0432.CCR-13-2686.

Gulino, et al. 2004. Altered leukocyte response to CXCL12 in patients with warts hypogammaglobulinemia, infections, myelokathexis (WHIM) syndrome. *Blood.* 104:444-452.

Hendrix, et al. 2004. Safety, Pharmacokinetics, and Antiviral Activity of AMD3100, a Selective CXCR4 Receptor Inhibitor, in HIV-1 Infection. *J Acquir Immune Defic Syndr.* 37:1253-1262.

Hernandez et al., Mutations in the chemokine receptor gene CXCR4 are associated with WHIM syndrome, a combined immunodeficiency disease. Nature Genetics 2003; 34:70-74.

Kawai, et al. 2005. Enhanced function with decreased internalization of carboxy-terminus truncated CXCR4 responsible for WHIM syndrome. *Exp Hematol.* 33:460-468.

Kawai and Malech; 2009. WHIM syndrome: congenital immune deficiency disease. *Curr Opin Hematol.* 16:20-26.

Kawai, et al.; WHIM syndrome myelokathexis reproduced in the NOD/SCID mouse xenotransplant model engrafted with healthy human stem cells transduced with C-terminus-truncated CXCR4. Blood. 2007; 109:78-84. Epub 2006 Aug. 31.

Lagane, et al. 2008. CXCR4 dimerization and beta-arrestin-mediated signaling account for the enhanced chemotaxis to CXCL12 in WHIM syndrome. *Blood.* 112:34-44.

Lapidot and Petit; 2002. Current understanding of stem cell mobilization: the roles of chemokines, proteolytic enzymes, adhesion molecules, cytokines, and stromal cells. *Exp Hematol.* 30:973-981.

Ma et al. 1999. The chemokine receptor CXCR4 is required for retention of B lineage and granulocytic precursors in the bone marrow microenvironment. *Immunity.* 10:463-471.

Martin et al. Births in the United States, 2013. National Center for Health Statistics Data Brief. No. 175: December 2014.

McCormick, et al. 2009. Impaired recruitment of Grk6 and beta-Arrestin 2 causes delayed internalization and desensitization of a WHIM syndrome-associated CXCR4 mutant receptor. *PLoS One.* 4:e8102.

a—McDermott, et al.; The CXCR4 antagonist plerixafor corrects panleukopenia in patients with WHIM syndrome. Blood. 2011; 118:4957-62.

b—McDermott, et al; A phase 1 clinical trial of long-term, low-dose treatment of WHIM syndrome with the CXCR4 antagonist plerixafor. Blood. 2014; 123:2308-16.

Mosi, et al. 2012. The molecular pharmacology of AMD11070: An orally bioavailable CXCR4 HIV entry inhibitor. *Biochem Pharmacology.* 83:472-479.

Moyle, et al.; Proof of Activity with AMD11070, an Orally Bioavailable Inhibitor of CXCR4-Tropic HIV Type 1. Clin Infect Dis. 2009; 48:798-805.

Nyunt, et al. Pharmacokinetic Effect of AMD070, an Oral CXCR4 Antagonist, on CYP3A4 and CYP2D6 Substrates Midazolam and Dextromethorphan in Healthy Volunteers. J Acquir Immune Defic Syndr. 2008; 47:559-565.

Stone, et al.; Multiple-Dose Escalation Study of the Safety, Pharmacokinetics, and Biologic Activity of Oral AMD070, a Selective CXCR4 Receptor Inhibitor, in Human Subjects. Antimicrob Agents Chemother. 2007; 51:2351-2358.

Ward and Dale; Genetic and molecular diagnosis of severe congenital neutropenia. Curr Opin Hematol. 2009; 16:9-13.

Wong, 2008. Comparison of the potential multiple binding modes of bicyclam, monocyclam, and noncyclam small molecule CXC chemokine receptor 4 inhibitors. *Mol Pharmacol.* 74:1485-1495.

Zlotnik and Yoshie 2000. Chemokines: a new classification system and their role in immunity. *Immunity.* 12:121-127.

Zuelzer: "Myelokathexis"—A New Form of Chronic Granulocytopenia. Report of a case. *N Engl J Med* 1964, 270:699-704.

Study Reports

A 28 day Oral (Capsule) Toxicity Study in the Male and Female Beagle Dog with a 14 day Recovery (Study CTBR77401): November 2003.

Pharmacology & Toxicology of AMD11070: Hematological Effects in the Male Beagle Dog. AnorMED, Inc. Mach 18, 2003 (Study No. AOM0031).

Hematological Effects of AMD11070 in Mice. Indiana University School of Medicine. Mar. 14, 2003 (Study No. AOM0033).

ACTG (DIAIDS) Protocol A5210. Unpublished data.

Internet References

George Diaz, Virginia Gulino. Whim syndrome. *Orphanet Encyclopedia.* June 2004; http://www.orpha.net/data/patho/GB/uk-Whim.pdf NORD (National Organization for Rare Diseases) 2015: https://rarediseases.org/rare-diseases/whim-syndrome Office of Rare Diseases: https://rarediseases.info.nih.gov/gard/9297/whim-syndrome/resources/1

Orphanet, WHIM Syndrome: http://www.orpha.net/consor/www/cgi-bin/OC_Exp.php?lng=EN&Expert=51636 Last Update October 2014

US Census Bureau: http://www.census.gov/quickfacts/table/PST045214/00 Last Revised June 2015

We claim:

1. A method for treating WHIM syndrome in a patient in need thereof, comprising administering to the patient about 200 mg, about 250 mg, about 300 mg, about 400 mg, about 450 mg, about 500 mg, or about 600 mg of X4P-001 or a pharmaceutically acceptable salt or composition thereof per day in a single or divided dose.

2. The method of claim 1, wherein the X4P-001 or a pharmaceutically acceptable salt thereof is administered in a dose of about 400 mg per day in a single or divided dose.

3. The method of claim 1, wherein the patient exhibits warts.

4. The method of claim 1, wherein cells taken from the patient exhibit expression of a mutant form of CXCR4.

5. The method of claim 1, wherein cells taken from the patient exhibit increased expression of CXCR4.

6. The method of claim 1, further comprising the step of obtaining a biological sample from the patient and measuring the amount of a disease-related biomarker.

7. The method of claim 6, wherein the biological sample is a blood sample.

8. The method of claim 7, wherein the disease-related biomarker is circulating CXCR4, SDF-1α/CXCL12, or GRK3 (G protein coupled receptor kinase 3).

9. The method of claim 2, wherein the X4P-001 or a pharmaceutically acceptable salt or composition thereof is administered orally once per day.

10. The method of claim 2, wherein the X4P-001 or a pharmaceutically acceptable salt or composition thereof is administered orally twice per day.

11. The method of claim 9, wherein the patient is in a fasted state when the X4P-001 or a pharmaceutically acceptable salt thereof is administered.

12. The method of claim 2, wherein the patient originally exhibited ANC less than 600/μL and/or ALC less than 1000/μL before treatment with X4P-001 or a pharmaceutically acceptable salt thereof.

13. The method of claim 2, wherein the patient originally exhibited ANC less than 400/μL before treatment with X4P-001 or a pharmaceutically acceptable salt thereof on at least two independent blood samples collected over a period of up to 14 days.

14. The method of claim 2, wherein the patient originally exhibited ANC less than 400/μL and/or ALC less than 650/μL before treatment with X4P-001 or a pharmaceutically acceptable salt thereof on at least two independent blood samples collected over a period of up to 14 days.

15. The method of claim 13, wherein the method results in increases in ANC levels to at least about 600/μL on at least 85% of assessments.

16. The method of claim 13, wherein the method results in increases in ALC to at least about 1000/μL on at least 85% of assessments.

17. The method of claim 13, wherein the method results in improved levels of protective antibody in the patient in response to a vaccine.

18. The method of claim 13, wherein the method results in at least 50% less respiratory tract infections.

19. The method of claim 13, wherein the method results in increased levels of total circulating WBC, neutrophils, and/or lymphocytes to at least 1.4× baseline.

* * * * *